(12) United States Patent
Laan Van Der et al.

(10) Patent No.: US 8,637,101 B2
(45) Date of Patent: Jan. 28, 2014

(54) LIPASES WITH HIGH SPECIFICITY TOWARDS SHORT CHAIN FATTY ACIDS AND USES THEREOF

(75) Inventors: Jan Metske Laan Van Der, Breda (NL); Yulia M. Efimova, Delft (NL); Karin Turk, Vienna (AT); Albertus Alard Van Dijk, Vlaardingen (NL); Natalja Alekseevna Cyplenkova, legal representative, Vlaardingen (NL); Margot Elisabeth Francoise Schooneveld-Bergmans, Delft (NL); Arie Gerrit Terdu, Strijen (NL); Arjen Sein, Leiden (NL)

(73) Assignee: DSM IP Assets B.V., Heerlen (NL)

( * ) Notice: Subject to any disclaimer, the term of this patent is extended or adjusted under 35 U.S.C. 154(b) by 216 days.

(21) Appl. No.: 12/919,768

(22) PCT Filed: Feb. 26, 2009

(86) PCT No.: PCT/EP2009/052299
§ 371 (c)(1),
(2), (4) Date: May 9, 2011

(87) PCT Pub. No.: WO2009/106575
PCT Pub. Date: Sep. 3, 2009

(65) Prior Publication Data
US 2011/0262591 A1  Oct. 27, 2011

(30) Foreign Application Priority Data

Feb. 29, 2008 (EP) .................................. 08102175
Mar. 31, 2008 (EP) .................................. 08103246
Jul. 15, 2008 (EP) .................................. 08160388
Jul. 16, 2008 (EP) .................................. 08160545
Aug. 7, 2008 (EP) .................................. 08162023

(51) Int. Cl.
| C12N 1/00 | (2006.01) |
|---|---|
| C12N 1/14 | (2006.01) |
| C12N 1/15 | (2006.01) |
| C12N 1/20 | (2006.01) |
| C12N 1/21 | (2006.01) |
| C12N 9/00 | (2006.01) |
| C12N 9/14 | (2006.01) |
| C12N 9/16 | (2006.01) |
| C12N 9/18 | (2006.01) |
| C12N 9/20 | (2006.01) |
| C12N 15/09 | (2006.01) |
| C12N 15/55 | (2006.01) |
| A23C 19/032 | (2006.01) |
| A23C 9/12 | (2006.01) |
| A21D 8/04 | (2006.01) |
| C12N 15/63 | (2006.01) |
| C12N 15/74 | (2006.01) |
| C12N 15/80 | (2006.01) |
| C12N 15/70 | (2006.01) |
| C12N 15/79 | (2006.01) |

(52) U.S. Cl.
USPC ............ 426/35; 426/391; 426/442; 426/496; 426/520; 426/523; 426/34; 426/390; 426/42; 426/49; 426/665; 426/7; 426/36; 426/40; 426/656; 426/580; 426/549; 426/556; 435/69.1; 435/196; 435/197; 435/198; 435/195; 435/320.1; 435/243; 435/252.1; 435/252.3; 435/254.1; 435/254.11; 435/254.3; 435/41; 435/134; 435/183; 536/23.2

(58) Field of Classification Search
None
See application file for complete search history.

(56) References Cited

U.S. PATENT DOCUMENTS

| 4,065,580 | A |  | 12/1977 | Feldman et al. |
|---|---|---|---|---|
| 6,143,545 | A | * | 11/2000 | Clausen et al. ............... 435/198 |
| 6,506,588 | B2 | * | 1/2003 | Tsutsumi et al. ............ 435/198 |
| 7,312,062 | B2 | * | 12/2007 | Bojsen et al. ................. 435/196 |
| 2004/0001819 | A1 |  | 1/2004 | Bolen et al. |
| 2005/0059130 | A1 |  | 3/2005 | Bojsen et al. |
| 2005/0287250 | A1 |  | 12/2005 | Olsen et al. |

FOREIGN PATENT DOCUMENTS

| WO | 98/26057 | 6/1998 |
|---|---|---|
| WO | 98/44804 | 10/1998 |
| WO | 98/45453 | 10/1998 |
| WO | 99/53769 | 10/1999 |
| WO | 00/32758 | 6/2000 |
| WO | 01/83770 | 11/2001 |
| WO | 02/00852 | 1/2002 |
| WO | 02/03085 | 1/2002 |
| WO | 2004/004467 | 1/2004 |
| WO | 2005/087918 | 9/2005 |
| WO | 2007/087508 | 8/2007 |
| WO | 2008/006781 | 1/2008 |
| WO | 2008/025674 | 3/2008 |
| WO | 2008/079685 | 7/2008 |

OTHER PUBLICATIONS

Pleiss et al., Anatomy of lipase binding sites: the scissile fatty acid binding site, Chem. Phys. Lipids, 1998, 93, 67-80.*
Intarapichet, "Off-Flavors in Foods: 3. Chemical Changes," Suranaree J. Sci. Technol. 3:21-29, 1996.
Christen et al, "Enzymes and Food Flavor—A Review," Food Biotechnology, 8 (2&3), 167-190, 1994.
Bertram et al, "Characterization of Lipases and Esterases from Metagenomes for Lipid Modification," J Am Oil Chem Soc 85:47-52, 2008.
International Search Report for PCT/EP2009/052299, mailed Jun. 16, 2009.
Written Opinion for PCT/EP2009/052299, mailed Jun. 16, 2009.

* cited by examiner

*Primary Examiner* — Robert Mondesi
*Assistant Examiner* — Todd M Epstein
(74) *Attorney, Agent, or Firm* — Mile & Stockbridge, P.C.

(57) ABSTRACT

The present invention relates to novel polynucleotide sequences comprising genes that encode novel lipolytic enzymes, as well as functional equivalents of the gene or the amino acid sequences with high homology thereto. The invention also relates to methods of using these lipolytic enzymes in industrial processes, for example in the dairy or baking industry.

23 Claims, 1 Drawing Sheet

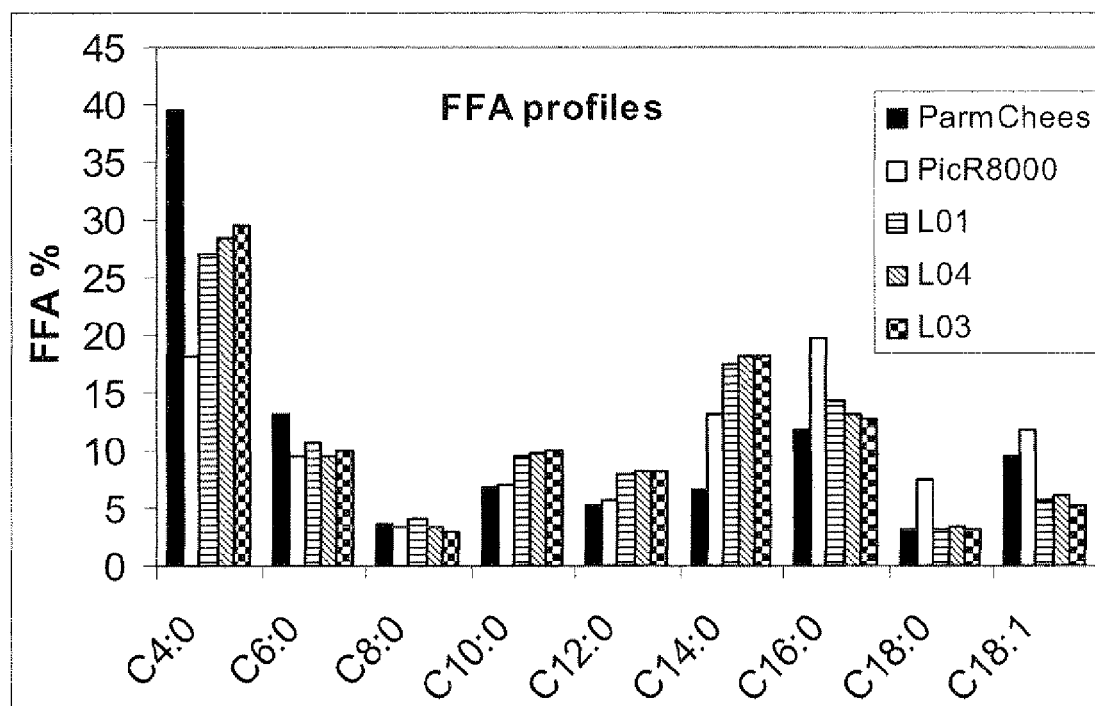

LIPASES WITH HIGH SPECIFICITY TOWARDS SHORT CHAIN FATTY ACIDS AND USES THEREOF

This application is the U.S. national phase of International Application No. PCT/EP2009/052299 filed 26 Feb. 2009 which designated the U.S. and claims priority to EP Patent Application Nos. 08102175.0 filed 29 Feb. 2008, 08103246.8 filed 31 Mar. 2008, 08160388.8 filed 15 Jul. 2008, 08160545.3 filed 16 Jul. 2008 and 08162023.9 filed 7 Aug. 2008, the entire contents of each of which are hereby incorporated by reference.

FIELD OF THE INVENTION

The invention relates to newly identified polynucleotide sequences comprising genes that encode a novel lipolytic enzyme. The invention features the full length coding sequence of the novel gene as well as the amino acid sequence of the full-length functional protein and functional equivalents of the gene or the amino acid sequence. The invention also relates to methods of using these proteins in industrial processes, for example in food industry, such as the dairy industry. Also included in the invention are cells transformed with a polynucleotide according to the invention suitable for producing these proteins and cells.

BACKGROUND OF THE INVENTION

Lipases are enzymes that catalyse the hydrolysis of ester bonds in lipid substrates, leading to the release of fatty acids. Lipases are used in the dairy applications for flavour generation, most importantly in cheese. Traditionally, ruminant lipase preparations are used derived from goat, kid goat, calf or lamb. These are derived from pregastric tissues from these ruminants and these lipase preparations are also referred to as pregastric esterases. Commercial preparations are in the market, such as the Piccantase® C, L, KG and K (DSM Food Specialties, The Netherlands). These lipases are used in the preparation of a variety of Italian, Spanish, Greek and French cheese. The development of a specific flavour profile in these types of cheese during ripening is largely due to the action of lipases on milk fat. Lipases catalyse hydrolysis of milk fat with generation of free fatty acids. Said fatty acids may have short chains (C4-C6 fatty acids, such as containing 4 or 6 carbon atoms, i.e. butyric, caproic acid) and medium to long chain (C12-C18 fatty acids). Subsequently free fatty acids can take part in chemical reactions, e.g. the formation of flavour compounds such as acetoacetate, beta-keto acids, methyl ketons, esters and lactones. Conversion of fatty acids in flavor components can be catalysed by the enzymes originating from the microbial population in cheese.

It is known that the type of free fatty acids released by lipases in cheese can be influenced by the type of lipases used. For example lipases that primarily release short chain fatty acids (e.g. C4 and C6 containing fatty acids) lead to the development of a piquant, sharp, spicy, tangy flavour, while release of medium to long chain fatty acids can lead to a soapy taste. Lipases find increasing use in other dairy applications than cheese, such as Enzyme modified Cheese (EMC; Wilkinson et al in Encyclopedia of Dairy Sciences, (2003; Fox et all eds, Academic Press) pp. 434-438) or the hydrolysis of butter fat and cream and their applications (Kilara in Enzyclopedia of Dairy Sciences, (2003; Fox et all eds, Academic Press) pp. 914-918).

Ruminant lipases are preferred over microbial lipases because of their specificity to release short chain fatty acids (C4-, C6-containing fatty acids) from milk fat. These compounds are either flavour compounds themselves or are converted into volatile esters with a particular flavour impact ((Liu et al, Int. Dairy J. 2004, 14, 923-945). An interesting issue is the composition of ruminant lipases, which is the topic of several papers (e.g. Addis et al Int. dairy J. (2005) 15, 1271-1278; Richardson et al, J. Dairy Sci. (1967) 50, 1061-1065; Addid et al Int. Dairy J. (2005) 15, 563-569; Hamosh Nutrition (1990) 6, 421-428; Calvo et al (2004) J. Dairy Sci. 87, 1132-1142). The data presented lead to the conclusion that most ruminant enzymes as probably mixtures of 2 or more lipases, and that variations in composition occur leading to changes in performance in cheese flavour formation. This variation is a driver for the industry to look for alternative enzyme sources with improved consistence. The occurrence of animal diseases like scrapie and mad cows disease is another driver for industry to look for alternatives. Further support comes from the desire to have easy acces to Kosher and Halal quality products. There is therefore a strong industrial desire for alternatives for animal derived lipases.

Patent application US2004/0001819 described the cloning and expression of kid pregastric esterase in the yeast *Pichia pastoris*. Although potentially interesting, the enzyme is poorly produced and in addition the free fatty acid release profile shifted to longer chain fatty acids, as compared to the original kid goat esterase. These two aspects made this enzyme unattractive because of poor economics and lack of performance in application. A preferred alternative would be microbial lipases or (microbial) lipases recombinantly produced by micro-organisms.

Several microbial lipases are in the market (for examples see e.g. Bjurlin et al, JAOCS (2001) 78, 153-160). The most important characteristic of microbial lipases for cheese application is their fatty acid release profile from milk fat, which should mimic as close as possible the animal derived lipases. Microbial lipases are, however, poor performers in this respect since they have a preference for the release of long chain (C12-C18) fatty acids relative to short chain fatty acids (C4, C6). This often leads to the formation of a soapy taste and not to the desired piquant flavour. Therefore, despite the fact that there is a considerable number of commercial microbial lipase preparations in the market there is still an industrial need for a non-animal derived lipase that can replace the animal derived lipases such as ruminant pregastric lipases.

DESCRIPTION OF THE FIGURES

FIG. 1: FFA profile generated by lipolytic enzymes L01, L03, L04 and by a commercial microbial lipase from *Rhizomucor miehei* (Piccantase® R8000) in Cheddar Cheese paste compared with the FFA profile of parmesan cheese.

OBJECT OF THE INVENTION

It is the object of the present invention to provide novel lipolytic enzymes which are suitable to be used in the dairy industry, more particularly in the manufacture of cheese or cheese-like products, in the lipolysis of butter fat or cream or in the production of enzyme-modified cheese. Furthermore, it is an object of the invention to provide novel polynucleotides encoding the novel lipolytic enzymes. A further object is to provide recombinantly produced lipolytic enzymes as well as recombinant strains producing these. Also fusion polypeptides are part of the invention as well as methods of making and using the polynucleotides and polypeptides according to the invention.

SUMMARY OF THE INVENTION

The present invention provides a novel lipolytic enzyme which is suitable to be used in the dairy industry. Surprisingly, the novel lipolytic enzyme is extremely suitable for use in flavour production by enzymatic modification of lipid-containing food ingredients, preferably cheese. The novel lipolytic enzyme can be advantageously used also in cheese ripening, in the manufacture of cheese-like products, in cream or butter fat modification. Furthermore the enzyme can be suitably used also in other food applications, such as in the manufacture of bakery products.

The invention furthermore provides novel polynucleotides encoding novel lipolytic enzymes.

The polynucleotide according to the invention comprises a nucleotide sequence selected from:
(a) the nucleotide sequence as set out in SEQ ID NO: 1 or a functional equivalent thereof having at least 90% homology to the nucleotide sequence of SEQ ID NO: 1;
(b) a nucleotide sequence which hybridizes with a polynucleotide being the complement of SEQ ID NO: 1 and wherein said sequence is at least 90% homologous to the nucleotide sequence of SEQ ID NO: 1;
(c) a nucleotide sequence encoding the mature polypeptide in the amino acid sequence according to SEQ ID NO: 2 or a functional equivalent thereof having at least 90% homology to the mature polypeptide in the amino acid sequence of SEQ ID NO: 2;
(d) a nucleotide sequence encoding an isolated polypeptide having lipolytic activity which is a functional equivalent of the mature polypeptide in the amino acid sequence of SEQ ID NO:2, which is at least 60% homologous to said mature polypeptide and which isolated polypeptide has a degree of specificity towards triglycerides $R_{spec}$ which is at least 0.7;
(e) a sequence which is degenerate as a result of the degeneracy of the genetic code to a sequence as defined in any one of (a), (b), (c), (d);
(f) a nucleotide sequence which is the complement of a nucleotide sequence as defined in (a), (b), (c), (d), (e).

In particular, the invention provides for polynucleotides having a nucleotide sequence that hybridizes preferably under high stringent conditions with a polynucleotide being the complement of SEQ ID NO: 1 and wherein said sequence is at least 90% homologous to the nucleotide sequence of SEQ ID NO: 1. Consequently, the invention provides polynucleotides that are at least 90%, preferably at least 91%, more preferably at least 92%, 93%, 94%, 95%, even more preferably at least 96%, 97%, 98% or 99% homologous to the sequence according to SEQ ID NO: 1.

In one embodiment such isolated polynucleotide can be obtained synthetically, e.g. by solid phase synthesis or by other methods known to the person skilled in the art.

In another embodiment the invention provides a lipolytic enzyme gene according to SEQ ID NO: 1 or functional equivalents that are still coding for the active enzyme.

Preferably the polynucleotide according to the invention is a DNA sequence.

The invention also relates to vectors comprising a polynucleotide sequence according to the invention and primers, probes and fragments that may be used to amplify or detect the DNA according to the invention.

In a further preferred embodiment, a vector is provided wherein the polynucleotide sequence according to the invention is operably linked with at least one regulatory sequence allowing for expression of the polynucleotide sequence in a suitable host cell. Preferably said suitable host cell is a filamentous fungus, more preferably *Aspergillus* species. Suitable strains belong to *Aspergillus niger*, oryzae or nidulans. Preferably the host cell is *Aspergillus niger*.

The invention also relates to recombinantly produced host cells that contain polynucleotides according to the invention.

The invention also provides methods for preparing polynucleotides and vectors according to the invention.

In another embodiment, the invention provides recombinant host cells wherein the expression of a polynucleotide according to the invention is significantly increased or wherein the production level of lipolytic activity is significantly improved.

In another embodiment the invention provides for a recombinantly produced host cell that contains heterologous or homologous DNA according to the invention and wherein the cell is capable of producing a functional lipolytic enzyme according to the invention, i.e. it is capable of expressing or preferably over-expressing a polynucleotide encoding for the lipolytic enzyme according to the invention, for example an *Aspergillus* strain comprising an increased copy number of a gene according to the invention.

In yet another aspect of the invention, an isolated polypeptide having lipolytic acitivity is provided. The polypeptides according to the invention comprises an amino acid sequence selected from:
(a) an amino acid sequence according to the mature polypeptide in the amino acid sequence according to SEQ ID NO: 2 or a functional equivalent thereof having an amino acid sequence at least 90% homologous to the mature polypeptide in the amino acid sequence according to SEQ ID NO: 2;
(b) a polypeptide which is a functional equivalent of the mature polypeptide in the amino acid sequence of SEQ ID NO: 2, which is at least 60% homologous to said mature polypeptide and which polypeptide has a degree of specificity towards triglycerides $R_{spec}$ which is at least 0.7;
(c) an amino acid sequence encoded by a polynucleotide according to the invention. Preferably the polypeptide according to the invention has a degree of specificity towards triglycerides $R_{spec}$ which is at least 0.7, preferably, at least 0.8, 0.9, 1.0, 1.1, 1.5, 1.7, 2, 2.5, 3.

In one embodiment the invention also relates to an isolated polypeptide having lipolytic activity which is a functional equivalent of the mature polypeptide in the amino acid sequence of SEQ ID NO: 2, which is at least 60%, 65%, 70%, 75%, 80%, 85%, 90%, 95% homologous to said mature polypeptide and which isolated polypeptide has a degree of specificity towards triglycerides $R_{spec}$ which is at least 0.7, preferably, at least 0.8, 0.9, 1.0, 1.1, 1.5, 1.7, 2, 2.5, 3. The invention also relates to a polynucleotide which comprises a polynucleotide encoding said polypeptide. $R_{spec}$ is defined further in the specification.

Fusion proteins comprising a polypeptide according to the invention are also within the scope of the invention. The invention also provides methods of making the polypeptides according to the invention.

The invention also relates to the use of the lipolytic enzyme according to the invention in any industrial process as described herein, more particular in the food industry, for example in the dairy or bakery industry.

DETAILED DESCRIPTION OF THE INVENTION

Polynucleotides

The present invention provides in a first aspect an isolated polynucleotide which comprises a nucleotide sequence selected from:

(a) a nucleotide sequence as set out in SEQ ID NO: 1 or a functional equivalent thereof having at least 90% homology to the nucleotide sequence of SEQ ID NO: 1;
(b) a nucleotide sequence which hybridizes with a polynucleotide being the complement of SEQ ID NO: 1 and wherein said sequence is at least 90% homologous to the nucleotide sequence of SEQ ID NO: 1;
(c) a nucleotide sequence encoding the mature polypeptide in the amino acid sequence according to SEQ ID NO: 2 or a functional equivalent thereof having at least 90% homology to the mature polypeptide in the amino acid sequence of SEQ ID NO: 2;
(d) a nucleotide sequence encoding an isolated polypeptide having lipolytic activity which is a functional equivalent of the mature polypeptide in the amino acid sequence of SEQ ID NO:2, which is at least 60% homologous to said mature polypeptide and which isolated polypeptide has a degree of specificity towards triglycerides $R_{spec}$ which is at least 0.7;
(e) a sequence which is degenerate as a result of the degeneracy of the genetic code to a sequence as defined in any one of (a), (b), (c), (d);
(f) a nucleotide sequence which is the complement of a nucleotide sequence as defined in (a), (b), (c), (d), (e).

In one embodiment, the present invention provides polynucleotides encoding lipolytic enzymes, having an amino acid sequence corresponding to the mature polypeptide in the amino acid sequence according to SEQ ID NO: 2 or functional equivalents having at least 90% homology to the amino acid sequence corresponding to the mature polypeptide in the amino acid sequence according to SEQ ID NO: 2.

In the context of the present invention "mature polypeptide" is defined herein as a polypeptide having lipolytic activity that is in its final form following translation and any post-translational modifications, such as N-terminal processing, C-terminal truncation, glycosylation, phosphorylation, etc. The process of maturation may depend on the particular expression vector used, the expression host and the production process. Preferably, the mature polypeptide is amino acids 34 to 304 in the amino acid sequence according to SEQ ID NO: 2. A "nucleotide sequence encoding the mature polypeptide" is defined herein as the polynucleotide sequence which codes for the mature polypeptide. Preferably the nucleotide sequence encoding the mature polypeptide is nucleotides 100 to 912 in SEQ ID NO: 1.

In another embodiment the invention relates to an isolated polynucleotide encoding an isolated polypeptide having lipolytic activity which is a functional equivalent of the mature polypeptide in the amino acid sequence of SEQ ID NO:2, which is at least 60%, 65%, 70%, 75%, 80%, 85%, 90%, 95% homologous to said mature polypeptide and which isolated polypeptide has a degree of specificity towards triglycerides $R_{spec}$ which is at least 0.7, preferably, at least 0.8, 0.9, 1.0, 1.1, 1.5, 1.7, 2, 2.5, 3. The invention also relates to a polynucleotide which comprises a polynucleotide encoding said polypeptide. $R_{spec}$ is defined further in the specification.

The invention provides polynucleotide sequences comprising the gene encoding the lipolytic enzyme as well as its coding sequence. Accordingly, the invention relates to an isolated polynucleotide comprising the nucleotide sequence according to SEQ ID NO: 1 or to variants such as functional equivalents thereof having at least 90% homology to SEQ ID NO: 1.

In particular, the invention relates to an isolated polynucleotide comprising a nucleotide sequence which hybridises, preferably under stringent conditions, more preferably under highly stringent conditions, to the complement of a polynucleotide according to SEQ ID NO: 1 and wherein preferably said sequence is at least 90% homologous to the nucleotide sequence of SEQ ID NO: 1.

More specifically, the invention relates to an isolated polynucleotide comprising or consisting essentially of a nucleotide sequence according to SEQ ID NO: 1.

Such isolated polynucleotide may be obtained by synthesis with methods known to the person skilled in the art.

As used herein, the terms "gene" and "recombinant gene" refer to nucleic acid molecules which may be isolated from chromosomal DNA, which include an open reading frame encoding a protein, e.g. a lipolytic enzyme. A gene may include coding sequences, non-coding sequences, introns and regulatory sequences. Moreover, a gene refers to an isolated nucleic acid molecule or polynucleotide as defined herein.

A nucleic acid molecule of the present invention, such as a nucleic acid molecule having the nucleotide sequence of SEQ ID NO: 1 or a functional equivalent thereof, can be isolated using standard molecular biology techniques and the sequence information provided herein. For example, using all or portion of the nucleic acid sequence of SEQ ID NO: 1 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual.2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 can be isolated by the polymerase chain reaction (PCR) using synthetic oligonucleotide primers designed based upon the sequence information contained in SEQ ID NO: 1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to the complement of the nucleotide sequences according to the invention can be prepared by standard synthetic techniques, e.g., using an automated DNA synthesizer.

In a preferred embodiment, an isolated nucleic acid molecule of the invention comprises the nucleotide sequence according to SEQ ID NO: 1. The sequence of SEQ ID NO: 1 encodes the polypeptide according to SEQ ID NO: 2 and the lypolitic enzyme according to the mature polypeptide in SEQ ID NO: 2. The lypolitic enzyme according to the mature polypeptide in the amino acid sequence according to SEQ ID NO: 2 is indicated as L01. The nucleotide sequence according to SEQ ID NO: 1 is indicated as DNA L01.

In another preferred embodiment, an isolated nucleic acid molecule of the invention comprises a nucleic acid molecule which is a complement of the nucleotide sequence shown in SEQ ID NO: 1 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a variant, such as a functional equivalent thereof, for example a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule according to the invention, e.g., the coding strand of a nucleic acid molecule according to the invention.

Also included within the scope of the invention are the complement strands of the polynucleotides according to the invention.

Nucleic Acid Fragments, Probes and Primers

A nucleic acid molecule according to the invention may comprise only a portion or a fragment of the nucleic acid sequence according to SEQ ID NO: 1, for example a fragment which can be used as a probe or primer or a fragment encoding a portion of a the protein according to the invention. The nucleotide sequence according to the invention allows for the generation of probes and primers designed for use in identifying and/or cloning functional equivalents of the protein according to the invention having at least 90% homology to the protein according to SEQ ID NO: 2. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence according to the invention.

Probes based on the nucleotide sequences according to the invention, more preferably based on SEQ ID NO: 1 can be used to detect transcripts or genomic sequences encoding the same or homologous proteins for instance in organisms. In preferred embodiments, the probe further comprises a label group attached thereto, e.g., the label group can be a radio-isotope, a fluorescent compound, an enzyme, or an enzyme cofactor. Such probes can also be used as part of a diagnostic test kit for identifying cells which express a protein according to the invention.

Identity & Homology

The terms "homology" or "percent identity" are used interchangeably herein. For the purpose of this invention, it is defined here that in order to determine the percent homology of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of squence comparison In D. Sankoff and J. B. Kruskal, (ed.), Time warps, string edits and macromolecules: the theory and practice of sequence comparison, pp. 1-44 Addison Wesley). The percent identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both aminoacid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of identity between a query sequence and a sequence of the invention is calculated as follows: Number of corresponding positions in the alignment showing an identical aminoacid or identical nucleotide in both sequences devided by the total length of the alignment after substraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http://www.ncbi.nlm.nih.gov/.

Hybridisation

As used herein, the term "hybridizing" is intended to describe conditions for hybridization and washing under which nucleotide sequences at least about 60%, 65%, 80%, 85%, 90%, preferably at least 93%, more preferably at least 95% and most preferably at least 98% homologous to each other typically remain hybridized to the complement of each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-standed cDNA clone).

Obtaining Full Length DNA from Other Organisms

In a typical approach, cDNA libraries constructed from other organisms, e.g. filamentous fungi, in particular from the species *Fusarium* can be screened.

For example, *Fusarium* strains can be screened for homologous polynucleotides with respect to SEQ ID NO:1, by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new nucleic acid sequence according to the invention, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, including cloning and expression vectors, comprising a polynucleotide sequence according to the invention encoding a polypeptide having lypolitic acitivity or a functional equivalent thereof according to the invention. The invention also pertains to methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990).

The term regulatory sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) optionally, a signal sequence capable of directing secretion of the polypeptide from the given host cell into a culture medium; (3) a DNA sequence of the invention encoding a mature and preferably active form of a polypeptide having lipolytic activity according to the invention; and preferably also (4) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e.g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e.g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. the polypeptide having lipolytic activity according to the invention, mutant forms the polypeptide, fragments, variants or functional equivalents thereof, fusion proteins, etc.).

The recombinant expression vectors of the invention can be designed for expression of the polypeptides according to the invention in prokaryotic or eukaryotic cells. For example, the polypeptides according to the invention can be produced in bacterial cells such as *E. coli* and *Bacilli*, insect cells (using baculovirus expression vectors), fungal cells, yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2μ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The nucleotide insert should be operatively linked to an appropriate promoter. Aside from the promoter native to the gene encoding the polypeptide of the invention, other promoters may be used to direct expression of the polypeptide of the invention. The promoter may be selected for its efficiency in directing the expression of the polypeptide of the invention in the desired expression host. Examples of promoters which may be useful in the invention include the phage lambda PL promoter, the E. coli lac, trp and tac promoters, the SV40 early and late promoters and promoters of retroviral LTRs, to name a few. Other suitable promoters will be known to the skilled person. In a specific embodiment, promoters are preferred that are capable of directing a high expression level of the polypeptides according to the invention in a fungus or yeast. Such promoters are known in the art.

A variety of promoters can be used that are capable of directing transcription in the host cells of the invention. Preferably the promoter sequence is derived from a highly expressed gene. Examples of preferred highly expressed genes from which promoters are preferably derived and/or which are comprised in preferred predetermined target loci for integration of expression constructs, include but are not limited to genes encoding glycolytic enzymes such as triosephosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases,β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), a-amylase (amy), amyloglucosidase (AG-from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase andtriosephosphate isomerase.

Examples of strong bacterial promoters are the α-amylase and SPo2 promoters as well as promoters from extracellular protease genes.

Promoters suitable for plant cells include nopaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

All of the above-mentioned promoters are readily available in the art.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, $2^{nd}$*,ed. Cold Spring Harbor Laboratory, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include, but are not limited to, those which confer resistance to drugs or which complement a defect in the host cell. They include e.g. versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g.URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase, subunit 9 (oliC), orotidine-5'-phosphatedecarboxylase (pvrA), the bacterial G418 resistance gene (this may also be used in yeast, but not in fungi), the ampicillin resistance gene (*E. coli*), the neomycin resistance gene (Bacillus) and the *E. coli* uidA gene, coding for β-glucuronidase(GUS). Vectors may be used in vitro, for example for the production of RNA or used to transfect or transform a host cell.

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria. Representative examples of appropriate host include bacterial cells, such as *E. coli, Streptomyces Salmonella typhimurium* and certain *Bacillus* species; fungal cells such as *Aspergillus* species, for example *A. niger, A. oryzae* and *A. nidulans*, such as yeast such as *Kluyveromyces*, for example *K. lactis* and/or *Puchia*, for example *P. pastoris*; insect cells such as *Drosophila* S2 and *Spodoptera* Sf9; animal cells such as CHO, COS and *Bowes melanoma*; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promotors suitable for use in the present invention include the promoters disclosed in WO-A1-2004/074468, which are hereby enclosed by reference.

Transcription of the DNA encoding the polypeptides of the present invention by higher eukaryotes may be increased by inserting an enhancer sequence into the vector. Enhancers are cis-acting elements of DNA, usually about from 10 to 300 by that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretation signal may be incorporated into the expressed gene. The signals may be endogenous to the polypeptide or they may be heterologous signals.

The polypeptide according to the invention may be produced in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having lypolitic activity comprising:
(a) the mature polypeptide in the amino acid sequence according to SEQ ID NO: 2 or a functional equivalent thereof having an amino acid sequence at least 90% homologous to the mature polypeptide in the amino acid sequence according to SEQ ID NO: 2;
(b) a polypeptide which is a functional equivalent of the mature polypeptide in the amino acid sequence of SEQ ID NO: 2, which is at least 60% homologous to said mature polypeptide and which polypeptide has a degree of specificity towards triglycerides $R_{spec}$ which is at least 0.7;
(c) an amino acid sequence encoded by a polynucleotide according to the invention.

Therfore the invention provides an isolated polypeptide having lypolitic activity comprising the mature polypeptide in the amino acid sequence according to SEQ ID NO: 2, preferably comprising amino acids 34-304 of SEQ ID NO: 2, and an amino acid sequence obtainable by expressing the polynucleotide of SEQ ID NO: 1 in an appropriate host. Also, a peptide or polypeptide being a functional equivalent and being at least 90% homologous to the mature polypeptide in the amino acid sequence according to SEQ ID NO: 2 is comprised within the present invention.

In another embodiment the invention also relates to an isolated polypeptide having lipolytic activity which is a functional equivalent of the mature polypeptide in the amino acid sequence of SEQ ID NO: 2, which is at least 60%, 65%, 70%, 75%, 80%, 85%, 90%, 95% homologous to said mature polypeptide and which isolated polypeptide has a degree of specificity towards triglycerides $R_{spec}$ which is at least 0.7, preferably, at least 0.8, 0.9, 1.0, 1.1, 1.5, 1.7, 2, 2.5, 3. $R_{spec}$ is defined later in the specification.

The above polypeptides are collectively comprised in the term "polypeptides according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" (or protein) is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual*, 2$^{nd}$, ed. Cold Spring Harbor Laboratory, Cold Spring Harbor Laboratory Press, Cold Spring Harbor, N.Y., 1989), By "isolated" polypeptide or protein is intended a polypeptide or protein removed from its native environment. For example, recombinantly produced polypeptides and proteins produced in host cells are considered isolated for the purpose of the invention as are native or recombinant polypeptides which have been substantially purified by any suitable technique such as, for example, the single-step purification method disclosed in Smith and Johnson, Gene 67:31-40 (1988).

As is known to the person skilled in the art it is possible that the N-termini of SEQ ID NO: 2 or of the mature polypeptide in the amino acid sequence according to SEQ ID NO: 2 might be heterogeneous as well as the C-terminus of SEQ ID NO: 2 or of the mature polypeptide in the amino acid sequence according to SEQ ID NO: 2, due to processing errors during maturation. In particular such processing errors might occur upon overexpression of the polypeptide. In addition, exoprotease activity might give rise to heterogeneity. The extent to which heterogeneity occurs depends also on the host and fermentation protocols that are used. Such C-terminal processing artefacts might lead to shorter polypeptides or longer polypeptides as indicated with SEQ ID NO: 2 or with the mature polypeptide in the amino acid sequence according to SEQ ID NO: 2. As a result of such errors the N-terminus might also be heterogeneous.

In a further embodiment, the invention provides an isolated polynucleotide encoding at least one functional domain of a polypeptide according to SEQ ID NO: 2 or of the mature polypeptide in the amino acid sequence according to SEQ ID NO: 2 which contain additional residues and start at position −1, or −2, or −3 etc. Alternatively, it might lack certain residues and as a consequence start at position 2, or 3, or 4 etc. Also additional residues may be present at the C-terminus, e.g. at position 347, 348 etc. Alternatively, the C-terminus might lack certain residues and as a consequence end at position 345, or 344 etc.

The lipolytic enzyme according to the invention can be recovered and purified from recombinant cell cultures by methods known in the art (Protein Purification Protocols, Methods in Molecular Biology series by Paul Cutler, Humana Press, 2004).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptide Fragments

The invention also features biologically active fragments of the polypeptides according to the invention.

Biologically active fragments of a polypeptide of the invention include polypeptides comprising amino acid sequences sufficiently identical to or derived from the amino acid sequence of the protein according to the invention (e.g., the mature polypeptide in the amino acid sequence of SEQ ID NO: 2), which include fewer amino acids than the full length protein but which exhibit at least one biological activity of the corresponding full-length protein, preferably which exhibit lipolytic activity. Typically, biologically active fragments comprise a domain or motif with at least one activity of the protein according to the invention. A biologically active fragment of a protein of the invention can be a polypeptide which is, for example, 5, 10, 15, 20, 25, or more amino acids in length shorter than the mature polypeptide in SEQ ID NO: 2, and which has at least 90% homology to the mature polypeptide in SEQ ID NO: 2. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the protein according to the invention.

Fusion Proteins

The polypeptides according to the invention or functional equivalents thereof, e.g., biologically active portions thereof, can be operably linked to a polypeptide not according to the invention (e.g., heterologous amino acid sequences) to form fusion proteins. A "polypeptide not according to the invention" refers to a polypeptide having an amino acid sequence corresponding to a protein which is not substantially homologous to the protein according to the invention. Such "non-polypeptide not according to the invention" can be derived from the same or a different organism. Within a fusion protein the polypeptide according to the invention can correspond to all or a biologically active fragment of the lipolytic enzyme according to the invention. In a preferred embodiment, a fusion protein comprises at least two biologically active portions of the protein according to the invention. Within the fusion protein, the term "operably linked" is intended to indicate that the polypeptide according to the invention and the polypeptide not according to the invention are fused in-frame to each other. The polypeptide not according to the invention can be fused to the N-terminus or C-terminus of the polypeptide.

For example, in one embodiment, the fusion protein is a fusion protein in which the amino acid sequences are fused to the C-terminus of the GST sequences. Such fusion proteins can facilitate the purification of the recombinant protein according to the invention. In another embodiment, the fusion protein according to the invention is a protein containing a heterologous signal sequence at its N-terminus. In certain host cells (e.g., mammalian and yeast host cells), expression and/or secretion of the protein according to the invention can be increased through use of a hetereologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by known methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purificaton of the fusion protein. The HA tag is another peptide useful for purification which corresponds to an epitope derived of influenza hemaglutinin protein, which has been described by Wilson et al., *Cell* 37:767 (1984), for instance.

Preferably, a fusion protein according to the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g, a GST polypeptide). A nucleic acid encoding for a polypeptide according to the invention can be cloned into such an expression vector such that the fusion moiety is linked in-frame to the protein according to the invention.
Functional Equivalents The terms "functional equivalents" and "functional variants" are used interchangeably herein.

Functional equivalents of the polynucleotide according to the invention are isolated polynucleotides having at least 60%, 65%, 70%, 75%, 80%, 85%, preferably at least 90% homology to the nucleotide sequence of SEQ ID NO: 1 and that encodes a polypeptide that exhibits at least a particular function of the lipolytic enzyme according to the invention, preferably a polypeptide having lipolytic activity. A functional equivalent of a polypeptide according to the invention least 90% homology to the mature polypeptide in the amino acid sequence of SEQ ID NO: 2 and that exhibits at least one function of a lipolytic enzyme according to the invention, preferably which exhibits lipolytic activity. Functional equivalents as mentioned herewith also encompass biologically active fragments having lipolytic activity as described above.

Functional equivalents of the polypeptide according to the invention may contain substitutions of one or more amino acids of the mature polypeptide of the amino acid sequence according to SEQ ID NO: 2 or substitutions, insertions or deletions of amino acids which do not affect the particular functionality of the enzyme. Accordingly, a functionally neutral amino acid substitution is a substitution in the mature polypeptide of the amino acid sequence according to SEQ ID NO: 2 that does not substantially alters its particular functionality. For example, amino acid residues that are conserved among the proteins of the present invention are predicted to be particularly unamenable to alteration. Furthermore, amino acids conserved among the proteins according to the present invention and other lipolytic enzymes are not likely to be amenable to alteration.

Functional equivalents of the polynucleotides according to the invention may typically contain silent mutations or mutations that do not alter the biological function of the encoded polypeptide. Accordingly, the invention provides nucleic acid molecules encoding polypeptides according to the invention that contain changes in amino acid residues that are not essential for a particular biological activity. Such proteins differ in amino acid sequence from the mature polypeptide in the amino acid sequence according to SEQ ID NO: 2 and yet retain at least one biological activity thereof, preferably they retain the lipolytic activity. In one embodiment a functional equivalent of the polynucleotide according to the invention comprises a nucleotide sequence encoding a polypeptide according to the invention, wherein the polypeptide comprises a substantially homologous amino acid sequence of at least about 60%, 65%, 70%, 75%, 80%, 85%, preferably at least 90%, 91%, 92%, 93%, 94%, 95%, 96%, 97%, 98%, 99% or more homologous to the mature polypeptide in the amino acid sequence according to SEQ ID NO: 2. In one embodiment the functional equivalent of the mature polypeptide in the amino acid sequence according to SEQ ID NO: 2 having at least 90% homology thereto is the polypeptide having an amino acid sequence according to the mature polypeptide in the amino acid sequence according to SEQ ID NO: 4 (indicated hereafter as L02), in another embodiment it is the polypeptide having an amino acid sequence according to the mature polypeptide in the amino acid sequence according to SEQ ID NO: 6 (indicated hereafter as L03), and in yet another embdodiment it is the polypeptide having an amino acid sequence according to the mature polypeptide in the amino acid sequence according to SEQ ID NO: 8 (indicated hereafter as L04). In a preferred embodiment the mature polypeptide in the amino acid sequence according to SEQ ID NO: 4, SEQ ID NO: 6 or SEQ ID NO: 8 respectively is amino acid sequence 34 to 304 in the amino acid sequence according to SEQ ID NO: 4, SEQ ID NO: 6 or SEQ ID NO: 8, respectively.

A functional equivalent of the polynucleotide according to the invention encoding a polypeptide according to the invention will comprise a polynucleotide sequence which is at least about 60%, 65%, 70%, 75%, 80%, 85%, preferably at least 90%, 91%, 92%, 93%, 94%, 95%, 96%, 97%, 98%, 99%, to or more homologous to a nucleic acid sequence according to SEQ ID NO 1.

In one embodiment a functional equivalent of the polynucleotide according to SEQ ID NO: 1 having at least 90% homology thereto is the polynucleotide having a nucleotide sequence according to SEQ ID NO: 3 (indicated as DNA L02), in another embodiment it is the polynucleotide having a nucleotide sequence according to SEQ ID NO: 5 (indicated as DNA L03), in yet another embodiment it is the polynucleotide having a nucleotide sequence according to SEQ ID NO: 7 (indicated as DNA L04). The polynucleotide sequence according to SEQ ID NO: 3 encodes the polypeptide according to SEQ ID NO: 4, the polynucleotide sequence according to SEQ ID NO: 5 encodes the polypeptide according to SEQ ID NO: 6, the polynucleotide sequence according toSEQ ID NO: 7 encodes the polypeptide according to SEQ ID NO: 8. In a preferred embodiment polynucleotide 100-912 in SEQ ID NO: 3, 5, 7 respectively encodes for the mature polypeptide in SEQ ID NO: 4, 6, 8.

An isolated polynucleotide encoding a protein homologous to the mature polypeptide in the amino acid sequence according to SEQ ID NO: 2 can be created by introducing one or more nucleotide substitutions, additions or deletions into the coding nucleotide sequences according to SEQ ID NO: 1 such that one or more amino acid substitutions, deletions or insertions are introduced into the encoded protein. Such mutations may be introduced by standard techniques, such as site-directed mutagenesis and PCR-mediated mutagenesis.

Nucleic acids encoding other family members having lipolytic activity, which thus have a nucleotide sequence that differs from SEQ ID NO: 1, 3, 5, 7 and which fullfills to the conditions mentioned above are within the scope of the invention. Moreover, nucleic acids encoding proteins having lipolytic activity, which have an amino acid sequence which differs from the mature polypeptide in the amino acid sequence SEQ ID NO: 2, 4, 6, 8 and which fulfill the conditions mention above are within the scope of the invention.

The polynucleotides according to the invention may be optimized in their codon use, preferably according to the methods described in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

Nucleic acid molecules corresponding to variants (e.g. natural allelic variants) and homologues of the polynucleotides according to the invention can be isolated based on their homology to the nucleic acids disclosed herein using the cDNAs disclosed herein or a suitable fragment thereof, as a hybridisation probe according to standard hybridisation techniques preferably under highly stringent hybridisation conditions.

In another aspect of the invention, improved proteins are provided. Improved proteins are proteins wherein at least one biological activity is improved if compared with the biological activity of the polypeptide having amino acid sequence according to SEQ ID NO: 2. Such proteins may be obtained by randomly introducing mutations along all or part of the coding sequence SEQ ID NO: 1, such as by saturation mutagenesis, and the resulting mutants can be expressed recombinantly and screened for biological activity. For instance, the art provides for standard assays for measuring the enzymatic activity of lipolytic enzymes and thus improved proteins may easily be selected.

In a preferred embodiment the polypeptide according to the invention has an amino acid sequence according to amino acids 34 to 304 in SEQ ID NO: 2. In another embodiment, the polypeptide is at least 90% homologous to the mature polypeptide in the amino acid sequence according to SEQ ID NO: 2 and retains at least one biological activity of a mature polypeptide in the amino acid sequence according to SEQ ID NO: 2, preferably it retains the lipolytic activity and yet differs in amino acid sequence due to natural variation or mutagenesis as described above.

In a further preferred embodiment, the protein according to the invention has an amino acid sequence encoded by an isolated nucleic acid fragment which hybridizes with a polynucleotide being the complement of SEQ ID NO: 1 and wherein said nucleotide sequence is at least 90% homologous to the nucleotide sequence of SEQ ID NO: 1, preferably under highly stringent hybridisation conditions.

Accordingly, the protein according to the invention is preferably a protein which comprises an amino acid sequence at least about 90%, 91% 92% 93% 94%, 95%, 96%, 97%, 98%, 99% or more homologous to the mature polypeptide in the amino acid sequence according to SEQ ID NO 2 and retains at least one functional activity of the mature polypeptide in the amino acid sequence according to SEQ ID NO: 2.

Functional equivalents of a protein according to the invention can also be identified e.g. by screening combinatorial libraries of mutants, e.g. truncation mutants, of the protein of the invention for lipolytic enzyme activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having a lipolytic activity according to the invention include, inter alia, (1) isolating the gene encoding the protein, or allelic variants thereof from a cDNA library; (2) in situ hybridization (e.g. FISH) to metaphase chromosomal spreads to provide precise chromosomal location of the gene as described in Verma et al., Human Chromosomes: a Manual of Basic Techniques, Pergamon Press, New York (1988); (3) Northern blot analysis for detecting expression of mRNA in specific tissues and/or cells and 4) probes and primers that can be used as a diagnostic tool to analyse the presence of a nucleic acid hybridisable to the probe in a given biological (e.g. tissue) sample.

Also encompassed by the invention is a method of obtaining a functional equivalent of a gene according to the invention. Such a method entails obtaining a labelled probe that includes an isolated nucleic acid which encodes all or a portion of the protein sequence according to the mature polypeptide in the amino acid sequence according to SEQ ID NO: 2 or a variant of any of them; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the gene according to the invention.

Host Cells

In another embodiment, the invention features cells, e.g., transformed host cells or recombinant host cells comprising a polynucleotide according to the invention or comprising a vector according to the invention.

A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like. Host cells also include, but are not limited to, mammalian cell lines such as CHO, VERO, BHK, HeLa, COS, MDCK, 293, 3T3, WI38, and choroid plexus cell lines. A number of vectors suitable for stable transfection of mammalian cells are available to the public, methods for constructing such cell lines are also publicly known, e.g., in Ausubel et al. (supra). Especially preferred are cells from filamentous fungi, in particular *Aspergillus* species such as *Aspergillus niger* or *oryzae* or *awamori*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein produced. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a recombinant host cell (e.g. transformed or transfected with an expression vector as described above) under conditions to provide for expression (by the vector) of a coding sequence encoding the polypeptide, and optionally recovering, more preferably recovering and purifying the produced polypeptide from the cell or culture medium. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide is produced as a secreted protein in which case the nucleotide sequence encoding a mature form of the polypeptide in the expression construct is operably linked to a nucleotide sequence encoding a signal sequence. Preferably the signal sequence is native (homologous) to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for yeast host cells are the signal sequences derived from yeast a-factor genes. Similarly, a suitable signal sequence for filamentous fungal host cells is e.g. a signal sequence derived from a filamentous fungal amyloglucosidase (AG) gene, e.g. the *A. niger* glaA gene. This may be used in combination with the amyloglucosidase (also called (gluco) amylase) promoter itself, as well as in combination with other promoters. Hybrid signal sequences may also be used with the context of the present invention.

Preferred heterologous secretion leader sequences are those originating from the fungal amyloglucosidase (AG) gene (glaA-both 18 and 24 amino acid versions e.g. from *Aspergillus*), the α-factor gene (yeasts e.g. *Saccharomyces* and *Kluyveromyces*) or the α-amylase gene (Bacillus).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free of enzymatic activities that might interfere with the applications, e.g. free from starch degrading, cellulose-degrading or hemicellulose degrading enzymes. This may be achieved by choosing a host which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In these instances, a fungal host organism should be selected.

The host cell may over-express the polypeptide, and techniques for engineering over-expression are well known. The host may thus have two or more copies of the encoding polynucleotide (and the vector may thus have two or more copies accordingly).

Therefore in one embodiment of the invention the recombinant host cell according to the invention is capable of expressing or overexpressing a polynucleotide or vector according to the invention.

According to the present invention, the production of the polypeptide of the invention can be effected by the culturing of a host cell according to the invention, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.).

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of 0.5-30 days. It may be a batch, continuous or fed-batch process, suitably at a temperature in the range of, for example, from about 0 to 45° C. and/or at a pH, for example, from about 2 to about 10. Preferred fermentation conditions are a temperature in the range of from about 20 to about 37° C. and/or at a pH of from about 3 to about 9. The appropriate conditions are usually selected based on the choice of the expression host and the protein to be produced.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

Use of the Lipolytic Enzyme in Industrial Processes

The invention also relates to the use of the lipolytic enzyme according to the invention in a number of industrial processes. Despite the long-term experience obtained with these processes, the lipolytic enzyme according to the invention features a number of significant advantages over the enzymes currently used. Depending on the specific application, these advantages can include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

Preferably the isolated polypeptide according to the invention having lipolytic activity can be used in the food industry, more preferably in food manufacturing.

Dairy Applications

In one preferred embodyment the polypeptide according to the invention can be used in the dairy industry.

In one embodiment the polypeptide according to the invention is used in the manufacture of a dairy product, preferably a cheese, cheese-like product, EMC, or of milk fat-derived free fatty acid mixtures, preferably to develop and/or intensify the flavour of the dairy product.

In the context of the present invention a 'dairy product' refers to any kind of milk-based product, including but not limited to cheese, butter, EMC, cream, dairy analog etcetera. Of particular interest in the present context are milk fat-containing products and their equivalents, including regular cheeses, cheese analogues, processed cheeses, butter, spreads, margarines, EMC, etc.

In a preferred embodiment, the dairy product is a cheese. The cheese may be of any variety, e.g. hard cheeses such as Chester, Danbo, Manchego, Saint Paulin, Cheddar, Monterey, Colby, Edam, Gouda, Muenster, Swiss type, Gruyere, Emmenthaler, Parmesan, Pecorino, Provolone, and Romano; curd-cheese such as Feta, pasta filata cheeses such as Mozzarella; processed cheese; white mould cheese such as Brie and Camembert; or blue mould cheeses such as Gorgonzola and Danish blue cheese, or fresh cheese such as e.g. Ricotta, Cream cheese, Neufchatel or Cottage cheese. Preferred types of cheese in this context are Parmesan, Pecorin, Provolone, Romano, Feta.

The term 'dairy analogues' refers to dairy-like products which contain fat (such as e.g. milk fat, e.g. cream) as part of the composition, and which further contain, as part of the composition, a non-milk constituent, such as e.g. vegetable oil.

The present invention also relates to a method for preparing a dairy product wherein an isolated polypeptide according to the invention is added to a dairy composition used in the production of a dairy product.

In the context of the present invention, a dairy composition may be a composition comprising milk and/or one or more milk components and/or milk fractions which is the starting composition in the production of the dairy product according to the invention or it may be an intermediate product in the production of the dairy product (e.g. curd or whey). The dairy compositon is a suitable substrate for the lipolytic enzyme and therefore the dairy composition will comprise at least milk fat and/or other fat, e.g. vegetable-derived fat. Lipolytic enzymes according to the invention are able to catalyse the hydrolysis of ester bonds in glycerides present in the dairy composition and they have therefore lipase activity. Glycerides are esters of glycerol and fatty acids. Triglycerides (also known as triacylglycerol or triacylglycerides) are mostly present in vegetable oils and animal fat. Lipases (EC 3.1.1.3) are defined herein as enzymes that hydrolyse one or more of the fatty acids from lipids, more specifically they hydrolyse the ester bond between fatty acid and hydroxyl groups of the glycerol.

A milk component may be any constituent of milk such as milk fat, milk protein, casein, whey protein, lactose. A milk fraction may be any fraction of milk such as e.g. skimmed milk, butter milk, whey, cream, butter, milk treated by ultrafiltration, milk powder, whole milk powder, butter milk powder, or skimmed milk powder. In the present context milk may be the lacteal secretion of any mammal. Thus, milk may be obtained by milking, e.g., cow, sheep, goat, buffalo, or camel.

The dairy product produced with the method of this aspect of the invention may be produced with any suitable process known in the art and the lipolytic enzyme will be added to the dairy compostion at any suitable step during the production of the dairy product under sitable conditions of e.g. enzyme concentration, temperature and time sufficient for the enzyme to exibit its lipolytic activity.

In one embodiment, the method according to the invention is a method for the production of cheese. In this case the method will comprise a step in which curd is formed by enzymatic coagulation of a dairy composition with rennet, or by acidic coagulation with food grade acid or acid produced by lactic acid bacteria growth and it is subsequently separated from the whey. Depending on the type of cheese to be produced, the production of cheese may further comprise processing of the curd and aging of the resulting cheese. The method to produce cheese according to this aspect of the invention will preferably include aging of the resulting cheese. The lipolytic enzyme can be added to a dairy composition in various stages of cheese preparation. Preferably, the enzyme is added to the milk prior to or together with the addition of a coagulant (e.g. chymosin). Addition at this point ensures a homogenous distribution of the enzyme throughout the cheese. Alternatively, the enzyme can be added in a later stage, e.g. to the curd, but this introduces the risk of inhomogeneous enzyme distribution in the cheese. For that reason, addition of the enzymes to the milk is preferred.

In another embodiment the method to produce a dairy product according to the present invention is the manufacture of milk fat-derived free fatty acid mixtures which is obtained by lypolisis of milk fat (e.g. butter fat or cream) to yield a free fatty acid mixture which can be for example used flavouring, e.g. in blue cheese flavour. These free fatty acid mixtures can be used as flavour ingredients in the production of other products, e.g. spreads, soups, dressings, snacks, chips, nachos, etcetera). Other lipase applications include the use in modified milk powder (Kilara in Encyclopedia of Dairy Sciences, (2003; Fox et all eds, Academic Press) pp. 914-918).

In yet another embodiment the method to produce a dairy product according to the present invention is a method to produce EMC. In this case the method can typically be performed using conditions known to those skilled in the art (see e.g. Ch. 2.12 in Industrial Enzymology, $2^{nd}$ Ed., Godfrey, West, Eds, MacMillan Press, London, 1996; Wilkinson et al in Encyclopedia of Dairy Sciences, (2003; Fox et all eds, Academic Press) pp. 434-438).

The amount of enzyme to be added in any one of the above-mentioned processes will depend on the enzyme activity and on the desired flavour effect in the final product. The amount to be used in an application can be determined by those skilled in the art by using a dose response curve. In this approach increasing amounts of enzyme are added to the dairy composition and subsequently the intensity of the flavour profile is analysed in the final product by a trained taste panel.

In a preferred embodiment of the use according to the invention or of the method to produce a dairy product according to the invention, the lipolytic enzyme according to the invention is used for development and/or intensification of flavour. Flavour development in the production of a dairy product is due, among others, to the action of enzymes, be it produced by microorganisms used during the production of the dairy product or specifically added during the manufacture, more specifically to the action of lipolytic and proteolytic enzymes.

Lipolytic enzymes are responsible for the lipolysis of milk fat present in the dairy product and the consequent release in the product of free fatty acid mixtures (hereafter indicated as FFA). The composition of the free fatty acid mixture is partially responsible for the final flavour of the dairy product. Starting from a substrate containing milk fat, a lipolytic enzyme will produce a specific FFA mixture of C4- to C18-containing free fatty acids wherein the relative amount of each component in the mixture will depend on the specificity of the enzyme towards the hydrolysis of specific triglyceride ester bonds involving the C4- to C18-containing fatty acids present in the triglyceride. For example a lipolytic enzyme which has high specifity for C4-containing fatty acids will preferentially hydrolyse triglyceride ester bonds of the trigyceril moiety with a C4-containing fatty acid rather than with C6- to C18-containing fatty acids and the relative content of C4-containing free fatty acid in the mixture will be higher if compared with the relative content of C6- to C18-containing free fatty acids. Furthermore the relative amount of each component in the mixture will also depend on the starting substrate and on the composition of the triglycerides present therein. Because every fatty acid is responsible for imparting to a product specific flavour characteristics, when a specific milk fat containing substrate is subjected to the action of a lipolytic enzyme under conditions of enzyme concentration, temperature and time sufficient for the enzyme to react, a specific FFA mixture is produced which gives rise to a specific flavour profile in the substrate. The specificity of several lipolytic enzymes towards the release of free fatty acids and therefore also the generated flavour profile can be compared with each other by determination of a FFA profile for each of the enzymes using the same substrate. A FFA profile gives the relative amount of each of C4- to C18-containing free fatty acids in respect of the total amount of free fatty acid released by the action of the lipolytic enzyme on the substrate. The FFA profile will generally depend from the starting substrate, on the specificity of the lipolytic enzyme towards the fatty acid sustituents in the lipid composition.

The degree of fat conversion (D) is calculated as follows (expressed in %):

D=[(total amount of FFA in the composition which has been treated with the lipolytic enzyme)/(total amount of FFA in the untreated composition)]/(total fatty acids present in the composition). The total amount of FFA and of total amount of fatty acid is expressed in mol/kg of substrate.

A suitable method to determine the FFA profile starting from a substrate is described in the Examples.

The lipolytic enzyme according to the invention has preferably a higher specificity towards the release of short chain free fatty acids, i.e. C4- to C10-containing free fatty acids, preferably C4-containing free fatty acids, if compared with the relase of longer chain free fatty acids, i.e. C12- to C18-containing free fatty acids. In a preferred embodiment the lipolytic enzyme according to the invention has a degree of specificity towards C4- to C10-containing free fatty acids if compared with C12- to C18-containing free fatty acids wich is expressed by the Specificity Ratio ($R_{spec}$) which is at least 0.7, preferably at least 0.8, 0.9, 1, 1.1, 1.5, 1.7, 2, 2.5, 3. Generally the $R_{spec}$ will be as high as possibly attainable.

$R_{spec}$ can be calculated as follows:

$R_{spec}$=ΣRelative C4-C10 content/ΣRelative C12-C18 content.

Wherein "ΣRelative C4-C10 content" is the sum of the relative content of C4-containing, C6-containing, C8-containing and 010-containing free fatty acids present in the composition which has been treated with the lipolytic enzyme and wherein "ΣRelative C12-C18 content" is the sum of the relative content of C12-containing, C14-containing, C16-containing and C18-containing free fatty acids present in the composition which has been treated with the lipolytic enzyme.

The "relative Cx content", wherein X can be any of 4, 6, 8, 10, 12, 14, 16, 18, corresponds to the percentage (%) of the amount of Cx-containing free fatty acid in the composition which has been treated with the lipolytic enzyme in respect with the total amount of free fatty acids present in the composition which has been treated with the lipolytic enzyme. The amount of FFA (or of free fatty acid) in the above mentioned formula is expressed in mol/kg.

The $R_{spec}$ is determined in a dairy composition made using young cheese (preferably Cheddar or Gouda cheese, preferably a young cheese with a ripening time of less than 2 weeks) and wherein the lipolytic enzyme is incubated under conditions (such as of dosage, incubation time and incubation temperature) that lead to a degree of fat convenrsion in the incubated sample comprised between 5%-25%, wherein the degree of fat conversion is calculated as indicated above.

The invention also relates to a dairy product which is obtainable by the method according to the invention In a preferred embodiment of the use of any isolated peptide according to the invention or of the method to produce a dairy product according to the invention the ΣRelative C4-C10 content/ΣRelative C12-C18 content is at least 0.7, preferably at least 0.8, 0.9, 1, 1.1, 1.5, 1.7, 2, 2.5, 3. In e.g. Parmesan cheese treatedwith ruminant pregastric esterase this ratio is approximately 1.7 (calculated from data from D. T. Lai, A. D. Mackenzie, C. J. O'Connor, K. W. Turner *J. Dairy Sci.* 80:2249-2257 (1997), page 2255). Relative C4-C10 content" and "ΣRelative C12-C18" have the same meaning as above.

In the art it is known that when a lipolytic enzyme acting on a milk-fat containing substrate primarily releases short chain fatty acids (e.g. C4 and C6 containing fatty acids) this leads to the development of a piquant, sharp, spicy, tangy flavour, while e.g. release of medium chain fatty acid can lead to a soapy taste.

Therefore In a preferred embodiment of the use of the invention or of the method to produce a dairy product according to the invention the sharp, tangy, spicy notes in the flavour profile of the dairy product are increased, preferably the soapy notes in the flavour profile of the dairy product are decreased.

In a further aspect the invention relates to a dairy product obtainable by the method to prepare a dairy product according to the invention. Examples of suitable dairy products are those mentioned in the previous aspects of the invention.

Bakery Applications

Another example of an industrial application of the lipolytic enzyme according to the invention in food is its use in baking applications to improve dough and/or baked product quality.

It has been surprisingly found that the lipolytic enzymes according to the invention can act upon several types of lipids, ranging from glycerides (eg. triglycerides), phospholipids, or glycolipids, such as galactolipids, in bakery applications.

More specifically the lipolytic enzymes according to the invention shows at least one of the following properties in situ when used in dough:
 a relatively low activity towards apolar lipids.
 a relatively high activity towards polar diacyl-lipids, at least towards diacyl galactolipids
 a relatively low activity towards polar monoacyl compounds, such as lysogalactolipids and lysophospholipids.

These unexpected properties are all found to be extremely advantageous when used as a replacer of chemical emulsifiers in dough.

Glycerides and lipases have been defined above.

Glycolipids (e.g. galactolipids) consist of a glycerol backbone with two esterified fatty acids in an outer (sn-1) and middle (sn-2) position, while the third hydroxyl group is bound to sugar residues such as in case of galactolipids a galactose, for example monogalacosyldiglyceride or digalactosyldiglyceride. Galactolipase (EC 3.1.1.26) catalyses the hydrolysis of one or both fatty acyl group(s) in the sn-1 and sn-2 positions respectively from a galactosyldiglyceride.

Phospholipids consist of a glycerol backbone with two esterified fatty acids in an outer (sn-1) and the middle (sn-2) position, while the third hydroxyl group of the glycerol is esterified with phosphoric acid. The phosphoric acid may, in turn, be esterified to for example an amino alcohol like ethanolamine (phosphatidylethanolamine), choline (phosphatidylcholine). Phospholipases are defined herein as enzymes that participate in the hydrolysis of one or more bonds in the phospholipids.

Several types of phospholipase activity can be distinguished which hydrolyse the ester bond(s) that link the fatty acyl moieties to the glycerol backbone:
 Phospholipase A1 (EC 3.1.1.32) and A2 (EC 3.1.1.4) catalyse the deacylation of one fatty acyl group in the sn-1 and sn-2 positions respectively, from a diacylglycerophospholipid to produce a lysophospholipid. This is a desirable activity for emulsifier replacement.
 Lysophospholipase (EC 3.1.1.5—also called phospholipase B by the Nomenclature Committee of the International Union of Biochemistry and Molecular Biology (Enzyme Nomenclature, Academic Press, New York, 1992)) catalyses the hydrolysis of the remaining fatty acyl group in a lysophospholipid. A phospholipase B has been reported from *Penicillium* notatum (Saito et al., 1991, Methods in Enzymology 197:446-456), which catalyses the deacylation of both fatty acids from a diacylglycerophospholipid and intrinsically possesses lysophospholipase activity. For emulsifier replacement lysophospholipase activity is less desirable, since this would result in deletion of the combination of a polair head and apolar tail, disabling the resulting product to influence surface properties. Surprisingly it was shown that the lipolytic enzyme according to the invention shows relatively low lysophospholipase activity in the dough.

Wheat flour contains approximately 2.2-2.9% lipids. The flour lipids can be divided into starch lipids (0.8-0.9%) and non-starch lipids (1.4-2.0%). Whereas the starch lipids consist mainly of polar lysophospholipids, the non-starch lipids consist of about 40% neutral triglycerides and 40% polar phospho- and glycolipids. For optimisation of the flour lipids fraction the lipase according to the invention is capable of hydrolysation of the polar lipids, being the phospholipids and glycolipids, more specifically the galactolipids in situ in the dough by adding the lipase according to the invention.

Baking enzymes may be used in a manifold of baked products. The term "baked products" is herein defined as to comprise bread products such as tin bread, loaves of bread, French bread as well as rolls, laminated dough products such as Danish pastry, croissants or puff pastry products, cakes, pies, muffins, yeast raised and cake doughnuts and the like.

The lipolytic enzyme according to the invention can for example be used in baked products. Baked products such as bread are prepared from a dough. Therefore in one embodiment of the invention provides the use of an isolated polypeptide according to the invention in the preparation of a dough and provides a dough comprising the polypeptide according to the invention. The invention also provides the preparation of a dough comprising the steps of adding the polypeptide according to the invention to at least one of the dough ingredients. Dough is usually made from the basic ingredients (wheat) flour, water and optionally salt. Depending on the baked products, other ingredients added may be sugars, flavours etc. For leavened products, primarily baker's yeast is used next to chemical leavening systems such as a combination of an acid (generating compound) and bicarbonate.

Yeast, enzymes and chemical additives are generally added separately to the dough.

Enzymes may be added in a dry, e.g. granulated form or in liquid form. The chemical additives are in most cases added in powder form. Also, processing aid compositions which are tailored to specific baking applications, may be composed of a dedicated mixture of chemical additives and enzyme.

The preparation of a dough from the ingredients and processing aids described above is well known in the art and comprises mixing of said ingredients and processing aids and one or more moulding and fermentation steps.

The preparation of baked products from such doughs is also well known in the art and may comprise moulding and shaping and further fermentation of the dough followed by baking at required temperatures and baking times. In one embodiment the invention provides a method to prepare a baked product comprising the step of baking the dough according to the invention. The invention also provides a baked product obtainable according to this method. Preferably the baked product according to the invention is bread.

The present invention also relates to methods for preparing a dough or a baked product comprising incorporating into the dough an effective amount of a lipolytic enzyme of the present invention which improves one or more properties of the dough or the baked product obtained from the dough relative to a dough or a baked product in which the polypeptide is not incorporated.

The phrase "incorporating into the dough" is defined herein as adding the lipolytic enzyme according to the invention to the dough, any ingredient from which the dough is to be made, and/or any mixture of dough ingredients from which the dough is to be made. In other words, the lipolytic enzyme according to the invention may be added in any step of the dough preparation and may be added in one, two or more steps. The lipolytic enzyme according to the invention is added to the ingredients of a dough that is kneaded and baked to make the baked product using methods well known in the art. See, for example, U.S. Pat. No. 4,567,046, EP-A-426, 211, JP-A-60-78529, JP-A-62-111629, and JP-A-63-258528.

The term "effective amount" is defined herein as an amount of the lipolytic enzyme according to the invention that is sufficient for providing a measurable effect on at least one property of interest of the dough and/or baked product.

The term "improved property" is defined herein as any property of a dough and/or a product obtained from the dough, particularly a baked product, which is improved by the action of the lipolytic enzyme according to the invention relative to a dough or product in which the lipolytic enzyme according to the invention is not incorporated. The improved property may include, but is not limited to, increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product and/or improved anti-staling of the baked product.

The improved property may be determined by comparison of a dough and/or a baked product prepared with and without addition of a polypeptide of the present invention in accordance with the methods of present invention which are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume and is evaluated by the ratio of height:width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g., TAXT2) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic.

The term "increased volume of the baked product" is measured as the volume of a given loaf of bread determined by an automated bread volume analyser (eg. BVM-3, TexVol Instruments AB, Viken, Sweden), using ultrasound or laser detection as known in the art.

The term "reduced blistering of the baked product" is defined herein as a visually determined reduction of blistering on the crust of the baked bread.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (eg. C-cell, Calibre Control International Ltd, Appleton, Warrington, UK).

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved anti-staling of the baked product" is defined herein as the properties of a baked product that have a reduced rate of deterioration of quality parameters, e.g., softness and/or elasticity, during storage.

The term "improved crispiness" is defined herein as the property of a baked product to give a crispier sensation than a reference product as known in the art, as well as to maintain this crispier perception for a longer time than a reference product. This property can be quantified by measuring a force versus distance curve at a fixed speed in a compression experiment using e.g. a texture analyzer TA-XT Plus (Stable Micro Systems Ltd, Surrey, UK), and obtaining physical parameters from this compression curve, viz. (i) force of the first peak, (ii) distance of the first peak, (iii) the initial slope, (iv) the force of the highest peak, (v) the area under the graph and (vi) the amount of fracture events (force drops larger than a certain preset value). Indications of improved crispness are a higher force of the first peak, a shorter distance of the first peak, a higher initial slope, a higher force of the highest peak, higher area under the graph and a larger number of fracture events. A crispier product should score statistically significantly better on at least two of these parameters as compared to a reference product. In the art, "cripiness" is also referred to as cripness, crunchiness or crustiness, meaning a material with a crispy, crunchy or crusty fracture behaviour.

The present invention provides a dough according to the invention having at least one of the improved properties selected from the group consisting of increased strength, increased elasticity, increased stability, reduced stickiness, and/or improved extensibility of the dough.

The invention also provides a baked product according to the invention having increased loaf volume. The invention provides as well a baked product according to the invention having at least one improved property selected from the group consisting of increased volume, improved flavour, improved crumb structure, improved crumb softness, improved crispiness, reduced blistering and/or improved anti-staling.

The term "dough" is defined herein as a mixture of flour and other ingredients firm enough to knead or roll. The dough may be fresh, frozen, pre-pared, or pre-baked. The preparation of frozen dough is described by Kulp and Lorenz in Frozen and Refrigerated Doughs and Batters.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pastries, croissants, pasta, noodles (boiled or (stir-)fried), pita bread, tortillas, tacos, cakes, pancakes, biscuits, cookies, doughnuts, bagles, pie crusts, steamed bread, and crisp bread, and the like.

Lipolytic enzymes of the present invention and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme such described in WO01/11974 and WO02/26044. Granulates and agglomerated powders may be prepared by conventional methods, e.g., by spraying the lipolytic enzyme according to the invention onto a carrier in a fluid-bed granulator. The carrier may consist of particulate cores having a suitable particle size. The carrier may be soluble or insoluble, e.g., a salt (such as NaCl or sodium sulphate), sugar (such as sucrose or lactose), sugar alcohol (such as sorbitol), starch, rice flour, wheat flour, corn grits, maltodextrins, soy. The lipolytic enzyme according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

The lipolytic enzyme according to the invention may also be incorporated in yeast comprising compositions such as disclosed in EP-A-0619947, EP-A-0659344 and WO02/49441.

For inclusion in pre-mixes of flour it is advantageous that the polypeptide according to the invention is in the form of a dry product, e.g., a non-dusting granulate, whereas for inclusion together with a liquid it is advantageously in a liquid form.

One or more additional enzymes may also be incorporated into the dough. Therefore the invention provides a baking enzyme composition comprising the lipolytic enzyme according to the invention and one or more additional enzymes. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling), beta-amylase, maltogenic amylase or non-maltogenic amylase, a cyclodextrin glucanotransferase, a protease, a peptidase, in particular, an exopeptidase (useful in flavour enhancement), transglutaminase, lipase (useful for the modification of lipids present in the dough or dough constituents so as to soften the dough), galactolipase, phospholipase, cellulase, hemicellulase, in particular a pentosanase such as xylanase (useful for the partial hydrolysis of pentosans, more specifically arabinoxylan, which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, hexose oxidase, e.g., a glucose oxidase, aldose oxidase, pyranose oxidase, lipoxygenase or L-amino acid oxidase (useful in improving dough consistency).

When one or more additional enzyme activities are to be added in accordance with the methods of the present invention, these activities may be added separately or together with the polypeptide according to the invention, optionally as constituent(s) of the bread-improving and/or dough-improving composition. The other enzyme activities may be any of the enzymes described above and may be dosed in accordance with established baking practices.

The present invention also relates to methods for preparing a baked product comprising baking a dough obtained by a method of the present invention to produce a baked product. The baking of the dough to produce a baked product may be performed using methods well known in the art. In one embodiment of the invention, the lipolytic enzymes of the invention are used to prepare laminated doughs for baked products with improved crispiness.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide of the present invention. The baking additive preferably has a narrow particle size distribution with more than 95% (by weight) of the particles in the range from 25 to 500 µm.

In dough and bread making the present invention may be used in combination with the processing aids defined hereinbefore such as the chemical processing aids like oxidants (e.g. ascorbic acid), reducing agents (e.g. L-cysteine), and/or emulsifiers (e.g. DATEM, SSL and/or CSL), and/or any precursors of emulsifiers which can be a substrate for the lipolytic enzyme of the invention and/or enzymatic processing aids such as oxidoreductases (e.g. glucose oxidase), polysaccharide modifying enzymes (e.g. α-amylase, hemicellulase, branching enzymes, etc.) and/or protein modifying enzymes (endoprotease, exoprotease, branching enzymes, etc.).

In one embodiment of the invention, the lipolytic enzyme according to the invention can be used to fully or partially replace the dough emulsifier DATEM.

In another embodiment the invention provides a baking composition comprising a lipolytic enzyme according to the invention and DATEM. DATEM is the acronym for diacetyl tartaric acid esters of mono- and diglycerides. One of the main components in DATEM may be 1-stearoyl-3-diacetyl-tartryl-glycerol. In a preferred embodiment the baking composition comprises DATEM and a lipolytic enzyme according to the invention selected from L01, L02, L03 and L04. Preferably the lipolytic enzyme is L01 or L02. It has been surprisingly found that a baking composition comprising a lipolytic enzyme according to the invention and DATEM has a synergistic effect on dough made using said composition and/or the baked product obtainable by baking said dough. The synergistic effect can be measured by making doughs or baked products with addition of DATEM or the lipolytic enzyme according to the invention separately and as a combination. The effects produced on at least one property of the dough or the baked products by using the baking composition on the one hand and DATEM alone or the lipolytic enzyme alone used each at a double dosage on the other hand can be compared. Synergy is found when the effect of the combination is better of both the effect produced by DATEM alone at double dosage and the lipolytic enzyme alone at double dosage. Synergy can be shown by e.g. improved stability of the dough, improved oven spring, improved crumb structure, improved crumb color, improved volume of the baked product. As an example, there is a synergistic effect when e.g. stability of a dough made by using a composition comprising 0.15% w/w (based on flour) of DATEM and 0.12 ppm lipolytic enzyme (i.e. 0.12 mg Bradford protein of lipolytic enzyme per kg of flour) is better than the stability of a dough made by using 0.3% w/w DATEM alone and is better than the stability of a dough made by using 0.24 ppm lipolytic enzyme alone.

The skilled person can easily determine suitable lipolytic enzyme and DATEM amounts to be used in the baking composition according to the invention. The optimal amounts of DATEM or of lipolytic enzyme respectively can first be determined whereby one or more properties of the dough or of the baking product produced with said dough are improved if compared with the properties of doughs or baked products obtained by neither adding DATEM nor lipolytic enzyme. Subsequently 30% to 50% w/w of optimal amount of each product can be used in the composition and the skilled person can verify by routine experimentation at which DATEM and lipolytic enzyme ratio in the composition a synergistic effect is observed.

In another preferred embodiment of the invention, the baking composition comprising DATEM and the lipolytic enzyme according to the invention is used in a method to produce a dough or a baked product of the invention.

The baking composition according to the invention may comprise next to a lipolytic enzyme according to the invention and to DATEM, one or more processing aids used in baking such as those mentioned above and/or one or more additional enzymes as described above. The baking composition comprising DATEM and the lipolytic enzyme according to the invention can be in any form suitable to be used in baking, such as in a solid or a liquid form. A composition in solid form can e.g. be a powder or a granulate. The liquid composition can be e.g. a water or a oil based compostion and optionally may be stabilized. The baking composition comprising the lipolytic enzyme according to the invention and DATEM may also be part of a pre-mix as defined above. The baking composition comprising the lipolytic enzyme according to the invention and DATEM can be added as such to the flour used to prepare the dough. Optionally it can be formed directly in the dough by separately adding the lipolytic enzyme according to the invention and DATEM in the appropriate amounts to the dough ingredients.

In another embodiment, the lipolytic enzyme according to the invention can be used in the production of cake and in the production of a batter from which a cake can be derived.

The lipolytic enzyme according to the invention can be used in all types of cake, including shortened cakes, such as for example pound cake and butter cake, and including foam cakes, such as for example meringues, sponge cake, biscuit cake, roulade, genoise and chiffon cake. Sponge cake is a type of soft cake based on wheat flour, sugar, baking powder and eggs (and optionally baking powder). The only fat present is from the egg yolk, which is sometimes added separately from the white. It is often used as a base for other types of cakes and desserts. A pound cake is traditionally prepared of one pound each of flour, butter, eggs, and sugar, optionally complemented with baking powder. In chiffon cake the butter/margarine has been replaced by oil. Sugar and egg yolk content has been decreased compared to pound or sponge cake and egg white content has been increased.

The lipolytic enzyme according to the invention can be used both in regular cakes and in cakes in which the amount of eggs and/or fat has been reduced. The reduction of the amount of eggs and/or fat which is possible differs per type of cake. The person skilled in the art knows the amount of eggs and/or fat which are regularly present in cake recipes and which is dependent on the type of cake. In general a reduction of the amount of eggs of at least 5% w/w can be reached. More preferably a reduction of the amount of eggs of at least 10% w/w can be reached, even more preferably a reduction of at least 15% w/w can be reached. It was shown that even a reduction of the amount of eggs used of at least 20% w/w can be reached. The reduction of the amount of eggs can be at least 30% w/w, 40% w/w or even at least 50% w/w.

In general a reduction of the amount of fat of at least 10% can be reached. More preferably a reduction of the amount of fat of at least 20% can be reached, even more preferably a reduction of at least 30% can be reached. It was shown that even a reduction of the amount of fat used of at least 50% can be reached.

In the International Patent Application number PCT/EP2008/051147 it has been disclosed that a phospholipase A can be used in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. In the same patent application it has also been disclosed that a phospholipase A can be used in the production of cake to enable reduction of the amount of eggs and/or fat used in the cake recipe. In particular it was shown that it was possible when using phospholipase A to reduce the amount of eggs and/or fat used in the recipe whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. The term at least maintaining is hereby used to indicate that a property is maintained or improved.

It has now been found that a composition comprising at least a phospholipase A and a lipolytic enzyme according to the invention can be used in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. It has also been found that a composition comprising at least a phospholipase A and a lipolytic enzyme according to the invention can be used in the production of cake to enable reduction of the amount of eggs and/or fat used in the cake recipe, preferably whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. In particular when a composition comprising at least a phospholipase A and a lipolytic enzyme according to the invention is used in cake where the amount of eggs and/or fat in the cake recipe has been reduced or in a cake comprising a regular amount of eggs and/or fat, one or more of the properties mentioned above can be further improved if compared with the use of the sole phospholipase A.

In this context all types of phospholipase A can be used, for example phospholipase A1 or phospholipase A2. Any type of phospholipase A1 can be used. Phospholipase A1 is widespread in nature, e.g. in microorganisms *E. coli*, in snake venoms, and in mammals in the brain, testis and liver. An example of a suitable commercially available phospholipase A1 is Lecitase Ultra™ (Novozymes). Any type of phospholipase A2 can be used. Preferably a phospholipase A2 is used. An example of a suitable commercially available phospholipase A2 is Cakezyme™ (DSM) or Lecitase 10L (Novozymes). A preferred phospholipase A2 is porcine pancreatic phospholipase A2 for example expressed in *Aspergillus niger* (Cakezyme™, DSM).

Measuring whether a property is maintained, improved or deteriorated in general is measured by preparing a batter and/or a cake in an original recipe, not containing any phospholipase A and any lipolytic enzyme according to the invention and by preparing other batters and/or cakes in a recipe containing phospholipase A, optionally less eggs and/or fat and optionally the lypolitic enzyme according to the invention and comparing a certain property. In case the properties of the two batters or cakes to be compared are substantially the same, the property is maintained, in case they differ either an improvement or a deterioration has taken place. For all mentioned properties below a measurement method has been given as well as an indication when a property can be considered as improved.

The batter viscosity can be measured with a Faringraph by standard methods according to the International Association of Cereal Chemistry (ICC) and the American Association of Cereal Chemistry (AACC 54-2, ICC 115). Whether e.g. the batter viscosity of a batter made with reduced amount of aggs and/or fat and comprising phospholipase A and a lipolytic enzyme according to the invention has improved or deteriorated in respect with the same batter but comprising either phospholipase A alone or neither phospholipase A nor lipolytic enzyme can for example be measured as follow. In case the batter viscosity of a batter containing a reduced amount of eggs and/or fat and prepared with phospholipase A and the lipolytic enzyme according to the invention is the same as that of e.g. the same batter prepared without phospholipase A and without the lipolytic enzyme or is the same as that of e.g. the same batter prepared with phospholipase A only the batter viscosity has been maintained. In case the batter viscosity has increased, it has improved.

The specific batter density can be measured by weighing a predetermined volume of batter. The specific density is improved if it is decreased.

The crumb softness of the cake is evaluated either empirically by the skilled test baker or measured by the use of a texture analyzer (e.g., TAXT2) as known in the art. Actually crumb firmness of the cake is measured as is known to the person skilled in the art. The crumb softness measured within 24 hours after baking is called initial crumb softness. The crumb softness more than 24 hours after baking is called crumb softness upon storage, and is also a measure for determining shelf life. In case the initial crumb softness has increased, it has improved. In case the crumb softness upon storage has increased, it has improved.

Crumb pore homogeneity of the cake can be evaluated empirically by the skilled test baker or by digital image analysis as known in the art (e.g. C-cell, Calibre Control International Ltd, Appleton, Warrington, UK). In case the deviation in pore size is small, the crumb is called more homogeneous. In case the deviation in pore size has become smaller, the property is improved.

Crumb pore diameter of the cake can be evaluated using digital image analysis as known in the art (e.g. C-cell, Calibre Control International Ltd, Appleton, Warrington, UK). In case the average crumb pore diameter decreases, the property is improved. Preferably, this is the case when at the same time the same cake volume is maintained.

The shelf-life of the cake can be measured by determining the resilience of the cake in time. This is part of the method to measure crumb softness, as is known to the person skilled in the art, whereby the relaxation of the cake is also measured by the use of a texture analyzer (e.g., TAXT2) as known in the art.

The volume of a given cake can be determined by an automated bread volume analyser (eg. BVM-3, TexVol Instruments AB, Viken, Sweden), using ultrasound or laser detection as known in the art. In case the volume is increased, the property is improved. Alternatively the cake height after baking in the same size tin is an indication of the cake volume. In case the cake height is increased, the cake volume has increased.

The emulsion stability of the batter can be determined by determining the cake height and visual analysis of the cake structure. In case the cake height has decreased, the emulsion stability of the batter has decreased. In case the cake structure is denser, the emulsion stability of the batter also has decreased.

It has been found that for example when adding a composition comprising a phospholipase A and a lipolytic enzyme according to the invention in a regular sponge cake or in a sponge cake containing a reduced amount of eggs, at least one or more of the following properties, e.g. an improved emulsion stability or the batter, a more efficient emulsification of the batter, an improved elasticity of the cake, an improved crumb softness of the cake, an improved volume of the batter can be observed if compared with the same cake or batter in which either only phospholipase A or either no phospholipase A and no lipolytic enzyme according to the invention can be used.

The present invention therefore provides the use of a composition comprising a lipolytic enzyme according to the invention and phospholipase A in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. The present invention also provides the use of a composition comprising a lipolytic enzyme according to the invention and phospholipase A in the production of cake to enable reduction of the amount of eggs and/or fat used in the cake recipe, preferably whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume.

The skilled person can easily determine suitable amounts of respectively phospholipase A and the lipolytic enzyme according to the invention to be used in the composition depending on the cake recipe and type.

Optionally one or more other ingredients can be present in the composition, next to phospholipase A and to the lipolytic enzyme according to the invention, e.g. to allow reduction of eggs and/or fat in the cake such as e.g. alternative protein sources, hydrocolloids, modified starch, yeast extract, calcium. Preferable ingredients are yeast extract, modified starch, calcium.

A yeast extract may be used which comprises at least 30% w/w 5'-ribonucleotides, preferably at least 34% w/w, 38% w/w, 40% w/w or 42% w/w, more preferably at least 44% w/w, 46% w/w, 48% w/w or at least 50% w/w 5'-ribonucleotides on the basis of sodium chloride free dry matter. It has been found that the use of such yeast extract not only improves the taste of the cake, but also has a surprising emulsifying effect, since upon its use, the viscosity of the batter improves.

In the context of the present invention, the phrase "5'-ribonucleotides" refers to the total amount of 5'-monophosphate ribonucleotides formed during RNA degradation, viz. 5'-monophosphate guanine (5'-GMP), 5'-monophosphate uracil (5'-UMP), 5'-monophosphate cytosine (5'-CMP), 5'-monophosphate adenine (5'-AMP), where 5'-AMP may be partially or completely converted into 5'-monophosphate inosine (5'-IMP). For example, in a yeast extract which comprises 30% w/w 5'-ribonucleotides on the basis of sodium chloride free dry matter, the total amount of 5'-GMP, 5'-UMP, 5'-CMP, 5'-AMP and 5'-IMP is 30% w/w on the basis of sodium chloride free dry matter. In a preferred embodiment, a yeast extract is used wherein the total amount of 5'-GMP plus 5'-IMP is at least 15% w/w, preferably at least 17% w/w, 19% w/w, 20% w/w or 21% w/w, more preferably at least 22% w/w, 23% w/w, 24% w/w or 25% w/w, on the basis of sodium chloride free dry matter. Due to the constitution of RNA, from which the 5'-ribonucleotides arise, 5'-GMP and 5'-IMP will always be present in approximately equal amounts in this embodiment. In the context of the present invention, weight percentage calculations of the 5'-ribonucleotides are based on the disodium salt heptahydrate thereof unless otherwise specified. All percentages are calculated on sodium chloride free dry matter. In the present invention, the phrase 'sodium chloride free dry matter' refers to the fact that for the calculation of the weight percentage the weight of any sodium chloride present in the yeast extract is excluded from the composition. The measurement of sodium chloride in the yeast extract and the above-mentioned calculation can be performed by methods known to those skilled in the art. An example of yeast extracts comprising 40% w/w 5'-ribonucleotides of which 20% w/w 5'-GMP plus 5'-IMP, weight percentages being based on sodium chloride free yeast extract dry matter, is sold under the trademark Maxarite® Delite (DSM Food Specialties, The Netherlands).

Modified starch can be used to reduce the amount of fat used in the cake recipe even further. All types of modified starch can be used, for example modified potato starch or modified wheat starch. Preferably modified potato starch is used, such as for example disclosed in U.S. Pat. No. 6,864,063. Most preferably modified potato starch is used which is obtained by treating potato starch with amylomaltase, An example of preferred modified potato starch is sold under the trademark Etenia® (Avebe Food). It has been surprisingly found that in cakes comprising a reduced amount of fat, e.g. as low as 30% w/w, and which are prepared using a combination of phospholipase A, a lipolytic enzyme according to the invention and modified potato starch, desired cake properties as those mentioned above, e.g. batter viscosity, are improved if compared with cakes produced by using 30% w/w less fat and no addition of phospholipase A, lipolytic enzyme and modified potato starch.

Calcium is preferably added to enhance the activity of the phospholipase A. It has been found especially advantageous to add approximately between 40-200 mg $CaCl_2.H_2O$ per 5,000 CPU Phospholipase A (hereafter indicated as PLA) to the cake recipe. Preferably, between 50 and 150 mg $CaCl_2.H_2O$ per 5,000 CPU PLA is added to the cake recipe and most preferably at least 90 mg $CaCl_2.H_2O$ per 5,000 CPU PLA. CPU (Chromogenic Phospholipase Unit=1 EYU (Egg Yolk Unit) is defined as the amount of enzyme that liberates 1 µmol of acid per minute from egg yolk at 40° C. and pH8.0. Substrate in this method: rac 1,2-dioctanoyldithio phosphatidylcholine measured spectrophotometric at 405 nm. Surprisingly, it has been found that the cake batter does not provide enough calcium for the phospholipase A to work efficiently. The invention further provides a method to prepare a batter or a method to prepare a cake wherein a compostion comprising a phospholipase A and a lipolytic enzyme according to the invention is added to the cake ingredients.

Typical ingredients of the cake are wheat flour, eggs and sugar. Optionally, baking powder, salt, water, emulsifiers (such as for example PGE's and monoglycerides), margarine, butter and/or oil are added (for example for pound cakes and muffins). A method to prepare a batter according to the invention preferably comprises the steps of:

a. preparing the batter of the cake by adding at least:
  i. sugar
  ii. flour
  iii. phospholipase A, the lipolytic enzyme according to the invention and eggs A method to prepare a cake according to the invention further comprises the step of b. baking the batter to yield a cake According to the above-mentioned method both cakes comprising a reduced amount of eggs and/or fat and cakes where no eggs and/or fat reduction has been applied can be prepared.

The person skilled in the art knows how to prepare a batter or a cake starting from cake ingredients. Optionally one or more other ingredients can be present in the composition e.g. to allow reduction of eggs and/or fat in the cake, such as protein sources, hydrocolloids, yeast extract, modified starch, calcium. Preferable ingredients are yeast extract, modified starch, calcium as defined above.

The invention further provides a cake or a batter obtainable by the method mentioned above. The invention also provides a baking composition, which may for example be used in the production of cake or batter, comprising a phospholipase A and a lipolytic enzyme according to the invention. This baking composition can also be used in dough products and baked products obtained from such dough. For example it can be used in dough products further containing eggs and in baked products derived thereof, such as brioche and panettone, both regular and with a reduced amount of eggs.

Said baking composition can also be part of a cake pre-mix comprising also flour and optionally other ingredients.

The above-mentioned industrial applications of the lipolytic enzyme according to the invention comprise only a few examples and this listing is not meant to be restrictive.

The lipolytic enzyme may conveniently be produced in microorganisms. In the above processes, it is advantageous to use lipolytic enzyme that are obtained by recombinant DNA techniques. Recombinant enzymes may be produced at a low cost price, high yield, free from contaminating agents like bacteria or viruses but also free from bacterial toxins or contaminating other enzyme activities.

Hereafter the invention is illustrated by the following non-limiting examples.

EXAMPLES

Example 1

Production of the Lipases of the Invention

The lipolytic enzymes L01, L02, L03, L04 encoded by the nucleotide sequences SEQ ID NO:1 (DNA L01), SEQ ID NO: 3 (DNA L02), SEQ ID NO: 5 (DNA L03), SEQ ID NO: 7 (DNA L04) as provided herein were obtained by constructing expression plasmids containing the DNA sequences, transforming an *Aspergillus niger* strain with such plasmid and growing the *A. niger* strains in the following way.

Fresh spores ($10^6$-$10^7$) of *A. niger* strains were inoculated in 20 ml CSL-medium (100 ml flask, baffle) and grown for 20-24 hours at 34° C. and 170 rpm. After inoculation of 5-10 ml CSL pre-culture in 100 ml CSM medium (500 ml flask, baffle) the strains were fermented at 34° C. and 170 rpm for 3-5 days.

Cell-free supernatants were obtained by centrifugation of the fermentation broth at 5000×g for 30 minutes at 4° C. The cell-free supernatants are stored at −20° C. until use. Optionally the supernatant can be filtered further over a GF/A Whatmann Glass microfiber filter (150 mm Ø) to remove the larger particles. If necessary the pH of the supernatant is adjusted to pH 5 with 4 N KOH and sterile filtrated over a 0.2 μm (bottletop) filter with suction to remove the fungal material.

The CSL medium consisted of (in amount per liter): 100 g Corn Steep Solids (Roquette), 1 g $NaH_2PO_4*H_2O$, 0.5 g $MgSO_4*7H_2O$, 10 g glucose*$H_2O$ and 0.25 g Basildon (antifoam). The ingredients were dissolved in demi-water and the pH was adjusted to pH 5.8 with NaOH or $H_2SO_4$; 100 ml flasks with baffle and foam ball were filled with 20 ml fermentation broth and sterilized for 20 minutes at 120° C. after which 200 μl of a sterile solution containing 5000 IU/ml penicillin and 5 mg/ml Streptomycin was added to each flask after cooling to room temperature.

The CSM medium consisted of (in amount per liter): 150 g maltose*$H_2O$, 60 g Soytone (pepton), 1 g $NaH_2PO_4*H_2O$, 15 g $MgSO_4*7H_2O$, 0.08 g Tween 80, 0.02 g Basildon (antifoam), 20 g MES, 1 g L-arginine. The ingredients were dissolved in demi-water and the pH was adjusted to pH 6.2 with NaOH or $H_2SO_4$; 500 ml flasks with baffle and foam ball were filled with 100 ml fermentation broth and sterilized for 20 minutes at 120° C. after which 1 ml of a sterile solution containing 5000 IU/ml penicillin and 5 mg/ml Streptomycin was added to each flask after cooling to room temperature.

Example 2

Purification of the Lipolytic Enzyme of the Invention

After thawing of the frozen cell-free supernatants obtained in example 1 the supernatants were centrifuged extensively at 4° C. to remove any solids. In order to remove low molecular weigth contaminations the supernatants were ultrafiltrated using a Millipore Labscale TFF system equipped with a filter with a 10 kDa cut-off. The samples were washed 3-5 times with 40 ml volumes of cold 100 mM phosphate buffer pH 6.0 including 0.5 mM $CaCl_2$. The final volume of the enzyme solution was 30 ml and is further referred to as "ultrafiltrate".

For further purification the ultrafiltrate can be applied to a MonoQ anion exchange column. The salt gradient was set to 1M NaCL over 20 column volumes. Buffers were a mixture of 70 mM Bis-TRIS and 50 mM TRIS. The pH was set with 0.1M HCl. Surprisingly it was observed that best results were obtained when the purification was performed at pH=9, where the lipase elutes at a conductivity of 35 mS/cm.

Total protein content of the samples was determined using the Bradford method (The Protein Protocols Handbook, $2^{nd}$ edition, Edited by J. M. Walker, Humana Press Inc, Totowa 2002, p 15-21).

Determination of the Lipolytic Enzyme Concentration by A280 and HPSEC

Alternatively the concentration of the lipolytic enzyme can be calculated from the extinction at 280 nm (A280) attributable to the lipolytic enzyme and the calculated molecular extinction coefficient of the lipolytic enzyme. Measurement of the A280 was performed in an Uvikon XL Secomam spectrophotometer (Beun de Ronde, Abcoude, The Netherlands).

The molecular extinction coefficient of an enzyme can be calculated from the number of tyrosine, tryptophan and cysteine residues per enzyme molecule (S. C. Gill and P. H. von Hippel, Anal. Biochem. 182, 319-326 (1989)). The molecular extinction coefficient of these amino acids are 1280, 5690 and 120 $M^{-1} \cdot cm^{-1}$ respectively. The number of tyrosine, tryptophan and cysteine residues in the lipolytic enzyme of the invention can be deduced from the protein sequences selected from the group consisting of SEQ ID NO:2, SEQ ID NO: 4, SEQ ID NO: 6, SEQ ID NO: 8. The calculations were carried out for SEQ ID NO: 2, SEQ ID NO: 4, SEQ ID NO: 6, SEQ ID NO: 8, comprising amino acids 34-304. The molar extinction coefficient for the lipolytic enzymes encoded by the above mentoned polynucleotide sequences is 35560 $M^{-1} \cdot cm^{-1}$ corresponding to an OD at 280 nm of 1.25 $cm^{-1}$ for 1 mg/ml. The calculated molecular weigth of the mature polypeptides is 28.4, 28.3, 28.4, 28.5 kD for lipases L01, L04, L03 and L02 respectively considering amino acids 34-304 only.

The extinction of the ultrafiltrate at 280 nm (A280) that is attributable to the lipolytic enzyme depends on the purity of the enzyme sample. This specific lipase content can be determined using HP-SEC (High Performance Size Exclusion Chromatography) with a TSK SW-XL column (300*7,8 mm; MW range 10-300 kDa). The elution buffer consisted of 25 mM sodium phosphate buffer pH 6.0 and was used at a flow of 1 ml/min. Samples of 5-100 μl were injected. The absorbance at 280 nm was measured.

The A280 attributable to the lipolytic enzyme of the invention was obtained from the ratio of the peak surface of the respective lipolytic enzyme peak in the chromatogram and the total surface of the peaks absorbing at 280 nm. The lipolytic enzyme concentration was then calculated by multiplying the A280 of sample by the ratio described above and divided by the calculated extinction coefficient for the lipolytic enzyme.

Example 3

Assays

Lipase activity was determined spectrophotometrically by using the chromogenic substrate p-nitrophenyl palmitate (pNPP, Sigma N-2752). In this assay the pNPP is dissolved in 2-propanol (40 mg pNPP per 10 ml 2-propanol (Merck 1.09634)) and suspended in 100 mM Acetate buffer pH=5.0 containing 1.0% Triton X-100 (Merck 1.12298) (5 ml substrate in 45 ml buffer). The final substrate concentration is 1.1 mM. The lipase is incubated with this substrate solution at 37° C. for 10 minutes. The reaction is stopped by addition of stop buffer 2% TRIS (Merck 1.08387)+1% Triton X-100 in a 1:1 ratio with respect to the reaction mixture and subsequently the formed p-nitrophenol (pNP) is measured at 405 nm. This assay can also be applied at different pH values in order to determine pH dependence of a lipase. It should be understood that at different pH values different buffers might be required or that different detergents might be necessary to emulsify the substrate. One lipase unit is defined as the amount of enzyme that liberates 1 micromole of p-nitrophenol per minute at the reaction conditions stated. It should be understood that it is not uncommon practice in routine analysis to use standard calibration enzyme solutions with known activity determined in a different assay to correlate activity a given assay with units as would be determined in the calibration assay.

Alternatively, lipase activity can be determined by using 2,3-mercapto-1-propanol-tributyrate (TBDMP) as a substrate. Lipase hydrolyses the thioester bond(s) of TBDMP thereby liberating butanoic acid and 2,3-mercapto-1-propanol-dibutyrate, 2,3-mercapto-1-propanol-monobutyrate or 2,3-mercapto-1-propanol. The liberated thiol groups are titrated inin a subsequent reaction with 4,4,-dithiodipyridine (DTDP) forming 4-thiopyridone. The latter is in a tautomeric equilibrium with 4-mercapthopyridine which absorbs at 334 nm. The reaction is carried out in 0.1 M acetate buffer pH 5.0 containing 0.2% Triton-X100, 0.65 mM TBDMP and 0.2 mM DTDP at 37° C. One lipase unit is defined as the amount of enzyme that liberates 1 micromole of 4-thiopyridone per minute at the reaction conditions stated.

In addition to spectrophotometric measurement lipase activity can also be determined using titrimetric measurement. For example the esterase activity of a lipolytic enzyme may be measured on tributyrin as a substrate according to Food Chemical Codex, Forth Edition, National Academy Press, 1996, p 803.

Activity Measurements

TABLE 1

Lipolytic enzyme activities in the cell-free supernatants as prepared in Example 1 (lipase activity was determined at pH 5 using p-nitrophenyl palmitate as a substrate. Lipase activity is given as units/mg total Bradford protein).

| Lipolytic enzyme | Lipase (units/mg) |
| --- | --- |
| L01 | 34 |
| L03 | 34 |
| L04 | 44 |
| L02 | 83 |

It should be further noted, that in this assay only a single substrate is present and that the activity number do not predict the actual activity in substrate mixtures as bread dough.

TABLE 2

Biochemical properties lipases L01, L02, L03 L04 Protein characterisation

| | MW apparent range | MW apparent deglycosylated | MW apparent glycosylated | pI apparent range | pI theoretical |
| --- | --- | --- | --- | --- | --- |
| L02 | 28-35 | 29 | 33 | 4.5-5.0 | 5.3 |
| L03 | 28-35 | 29 | 33 | 4.5-5.0 | 5.3 |
| L04 | 30-33 | 29 | 33 | 4.3-4.7 | 5.0 |
| L01 | 28-41 | 29 | 33-41 | 4.2-4.7 | 4.9 |

SDS-PAGE molecular weight estimation was performed with NuPage 4-12% MES Simply Blue Safe Stain on the ultrafiltrate samples. In order to deglycosylate the proteins, the protein sample was treated with PNGase-F (Roche Diagnostics GmbH, Mannheim Germany). Subsequently both treated and untreated sample were subjected to SDS-PAGE gel electrophoresis. Characterisation and handling of glycoproteins is extensively described in The Protein Protocols Handbook, $2^{nd}$ edition, Edited by J. M. Walker, Humana Press Inc, Totowa 2002, chapter VI.

The isoelectric point (pI) was determined by isoelectric focusing gel electrophoresis in comparison to IEF Marker 3-10 (Serva Electrophoresis GmbH, Heidelberg, Germany), containing marker proteins with a pI range from 3.5 to 10.7. If necessary, samples can be desalted by e.g. using protein desalting spin columns (Product number 89849, Pierce, Rockford, USA) as described by the manufacturer. Samples were then diluted 1:1 with Novex® IEF Sample Buffer pH 3-10 and subjected to isoelectric focusing gel electrophoresis using the Xcell SureLock™ Mini-Cell Electrophoresis system for Novex® IEF gels (Invitrogen Carlsbad, USA) as described by the manufacturer. After the run the gel was fixed with 12.5% TCA, washed and stained with SimplylBlue™ SafeStain (Invitrogen, Carlsbad, USA).

Determination of the Molecular Weight of L01 by Mass-spectroscopy (MS)

Lipase L01 was deglycosylated before MW analysis. Prior to deglycosylation a TCA precipitation was performed. TCA precipitation was performed by diluting the sample 1:1 in 20% TCA. The sample was incubated for 4 hours at 4° C. Proteins were pelleted by centrifugation at 13000 rpm for ten minutes at 4° C. The pellet was washed with acetone −20° C. and centrifuged again at 13000 rpm for ten minutes at 4° C. This washing step was repeated three times. The pellet was suspended in 100 mM NH4HCO3 and deglycosylation using N-glycosidase F (PNGase-F, Roche Diagnostics GmbH, Mannheim Germany) was performed at 37° C. overnight. The released sugar chains were removed by ultra filtration, using a 10 kDa cut-off centrifugal device (Pall).

The deglycosylated lipase L01 was analyzed by MS. The sample was directly infused on the LTQ-Orbitrap MS (Thermo). Six distinct protein masses could be calculated between 28 and 29 kDa. These protein masses, the corresponding residues of lipase L01 and their relative abundance compared to the most abundant form are shown in table 1.

TABLE 3

The calculated intact masses of the deglycosylated lipase L01. The relative abundance is compared to the most abundant form of 28435.7 Da, set to 100%.

| Molecular Weight (Da) | Relative Abundance (%) | Residues of L01 |
| --- | --- | --- |
| 28435.7 | 100 | 34-304 |
| 28250.6 | 61 | 34-303 −W C-term |
| 28707.8 | 32 | 31-304 +AVT N-term |
| 28520.7 | 28 | 31-303 −W & +AVT |
| 28912.9 | 21 | 34-307 +RRY C-term |
| 28163.5 | 19 | 34-302 −SW C-term |
| 29185.1 | 17 | 31-307 +AVT & +RRY |

The small differences in MW indicate that using SDS PAGE these forms will be observed as one single band at 28-29 kD. Both the N-terminus and the C-terminus exhibit heterogeneity, which might be caused by reduced processing specificity or by further proteolytic degradation in the production process after initial maturation. Because the deglycosylated lipases L02, L03, L04 show on SDS-PAGE a mobility that is virtually identical to the mobility of L01, it is concluded that L02, L03 and L04 undergo similar post-translational processing as observed for L01.

pH Optimum

The pH optimum dependence of the lipolytic enzyme can be determined by carrying out an assay that measures certain type of lipolytic activity at different pH values. The pH at which maximal activity is observed is the pH optimum of the particular enzyme. As the pH optimum might depend on the type of substrate and the applied assay conditions, it should be reestablished when different substrates are used or when assay conditions drastically change.

L01 has a broad pH optimum 6.5-9.5 using p-nitrophenylpalmitate as a substrate at 37° C. in phosphate buffer.

Example 4

Dairy Application—Free Fatty Acid Profile Generated by the Lipases According to the Invention in a Cheese-like System The FFA profile generated by L01, L03 and L04 polypeptides according to the invention and FFA profiles of a microbial lipase (Piccantase® R8000, a microbial lipase from *Rhizomucor miehei* from DSM Food Specialties, The Netherlands) (herewith abbreviated as PicR8000) after incubation with Cheddar cheese paste were compared. The FFA profile of Parmesan cheese as a gold standard is taken from D. T. Lai, A. D. Mackenzie, C. J. O'Connor, K. W. Turner *J. Dairy Sci.* 80:2249-2257 (1997), page 2255 (herewith abbreviated as ParmChees). The FFA profile of Cheddar cheese paste incubated with water instead of lipases was used as a negative control or blank in all experiments and it was not much different from the FFA profile of Cheddar cheese as known from literature, M. V. Arbige, P. R. Freund, S. C. Silver, J. T. Zelko, *Food Technology* 1986, pages 91-98.

The Cheddar cheese paste was prepared from young Cheddar cheese (i.e. with a time of ripening shorter than 2 weeks) by grating and mixing with water to final a moisture content 46.4% w/w (fat content on dry matter was 49.3% w/w). The Cheddar cheese paste was pasteurized for 5 min at +80° C., divided into small portions and stored at +4° C. until the use as a substrate for the lipolytic enzymes in this experiment.

Each of the tested lipases (solution in water) was added to a warm +40° C. portion of Cheddar cheese paste, thoroughly mixed and incubated for 1 and 4 days at +40° C. The lipases dosages were chosen in order to get a fat conversion ratio in the Cheddar cheese paste between 5-25%. In order to stop the lypolitic activity in the Cheddar cheese paste, samples were instantly frozen at −20° C. and stored frozen until the analysis.

All samples were analyzed with respect to their FFA profile. Determination of the released FFA in the Cheddar cheese pastes were carried out according to a standard method described in the art (Jong C., de and Badings H. T. J. *High Resolution Chromatography*, 13:84-98 (1990)). In short terms, after extraction of unreacted fat and FFA from the samples each FFA were isolated by solid-phase extraction method and the isolated FFA were analyzed by gas chromatography on a capillary column. The peaks on chromatograms were identified by comparison of the retention times with a standard mixture containing the same FFA. The FFA contents in the various samples were calculated from the peak areas of the individual FFA using internal standards that were added to the samples (with correction for detector response and extraction yield). The free fatty acids content were measured in mg of each free fatty acid per kg Cheddar cheese paste and further using molecular weight of FFA was recalculated in mmol per kg Cheddar cheese paste.

As a result, the free fatty acids profiles given in mmol/kg were used for calculation of the percent of fat conversion in each sample to verify that this is comprised between 5-25%. The degree of fat conversion was determined by correcting for background using the FFA profile of a blank measurement being Cheddar cheese paste incubated with water.

Therefore, the degree of fat conversion in each sample was determined as indicated in the description and assuming that Cheddar cheese paste contains a total amount of fatty acids of 1.19 mol/kg:

$$D = \frac{(\text{total amount of } FFA \text{ in sample} - \text{amount of } FFA \text{ acids in blank})}{1.19} * 100\%. \quad [1]$$

Using formula [1] the D was calculated for each samples and results are summarised in Table 4.

TABLE 4

| | Degree of fat conversion | |
|---|---|---|
| Lipase | D % 1 day | D % 4 days |
| L01 | 14.8 | 15.8 |
| L03 | 21.0 | 22.5 |
| L04 | 21.1 | 21.5 |
| PicR8000 | 6.2 | 10.0 |

As could be seen from Table 4 the D does not change significantly after 1 and 4 days of incubation time and enzymes dosing were in proper range.

In order to compare the specificity of lipases to release certain FFA independent to their dosages it is convenient to calculate the relative Cx content of each FFA (in mmol/kg of Cheddar cheese paste) to total FFA (in mmol/kg of Cheddar cheese paste) and thus FFA profiles are expressed in %. This method of comparison is well known to the person in the art and widely used in literature. Since it was found that FFA profiles of investigated samples do not change significantly between day 1 and day 4 the only the data for day 4 are presented in Table 5 and shown in FIG. 1.

The FFA profile of Parmesan Cheese is given as well, see D. T. Lai, A. D. Mackenzie, C. J. O'Connor, K. W. Turner *J. Dairy Sci.* 80:2249-2257 (1997), page 2255.

TABLE 5

| Relative Cx content in each sample | | | | | |
|---|---|---|---|---|---|
| | Relative Cx-content in each sample (expressed in mol %) | | | | |
| Cx-containing FFA | L03 | L01 | L04 | PicR8000 | ParmChees |
| C4:0 | 29.5 | 27.0 | 28.3 | 18.1 | 39.6 |
| C6:0 | 9.9 | 10.8 | 9.6 | 9.5 | 13.2 |
| C8:0 | 3.1 | 4.1 | 3.3 | 3.3 | 3.7 |
| C10:0 | 10.1 | 9.5 | 9.7 | 7.1 | 6.9 |
| C12:0 | 8.2 | 8.0 | 8.2 | 5.7 | 5.3 |
| C14:0 | 18.3 | 17.5 | 18.2 | 13.2 | 6.7 |
| C16:0 | 12.6 | 14.3 | 13.1 | 19.7 | 11.8 |
| C18:0 | 3.1 | 3.2 | 3.5 | 7.5 | 3.1 |
| C18:1 | 5.3 | 5.8 | 6.1 | 11.8 | 9.6 |

From Table 5 and FIG. 1 it is clear that FFA profile of Parmesan cheese is very different than that generated by microbial lipase PicR8000 which is marketed for production of sharp and piquant varieties of Italian cheeses, such as Provolone, Parmesan, Romano, (Technical Bulletin, DSM the Netherlands). It is generally known that microbial lipases are not short C4-C10 FFA specific and several examples including commercial preparations are available in the art. Until now PicR8000 is used as one of the microbial lipases that are able to release short FFA from milk fat.

Surprisingly it was found that lipases according the invention L01, L03 and L04 show in comparison with PicR8000 high specificity for the release of C4-containing free fatty acid. The FFA profile generated by these polypeptides is closer to the FFA profile of Parmesan cheese if compared with that of PicR8000. Specificity of the lipases can be compared using the specificity ratio $R_{spec}$ that can be calculated as:

$$R_{spec} = \frac{\sum C4 - C10}{\sum C12 - C18}$$

where "$\Sigma C4-C10$ and $\Sigma C12-C18$ are sums of relative FFA and are defined in the description. The $R_{spec}$ is determined for dairy composition which was made using young cheese (preferably Cheddar or Gouda cheese with a ripening time of less than 2 weeks) incubated with the lipolytic enzyme under conditions of dosage, incubation time and incubation temperature that lead to sufficient degree of fat conversion in the incubated samples comprised between 5%-25%, wherein the degree of fat conversion is calculated as indicated above. The values of the $R_{spec}$ for L01, L03, L04 and PicR8000 are given in Table 6.

TABLE 6

Specificity ratio $R_{spec}$ of lipases of invention L01, L03 and L04 in comparison with microbial lipase PicR8000 and Parmesan cheese.

|  | Parmesan cheese | PicR8000 | L03 | L04 | L01 |
|---|---|---|---|---|---|
| $R_{spec}$ | 1.7 | 0.62 | 1.11 | 1.04 | 1.05 |

As it can be seen the lipases according to the invention, L01, L03 and L04 show a high specificity for the release of C4- to 010-containing free fatty acids compare to microbial enzyme Piccantase® R8000 which is less specific.

Example 5

Baking Experiment

Full Scale Batard

The baking performance of the lipolytic enzymes L01-L04 was also tested in full scale batard. 2000 g of flour (Kolibri™), 47 g compressed yeast, 40 g salt, 50 ppm ascorbic acid, 2 ppm Bakezyme® P500 (fungal alpha-amylase), 15 ppm Bakezyme® HSP6000 (fungal hemicellulase) and 58% ml water was mixed in a Diosna mixer for 2 minutes at speed 1 and 71 Wh at speed 2, to a final dough temperature of 27° C. The dough was divided in 6 pieces of 350 g, rounded and proofed for 20 minutes at 32° C. and 90% relative humidity. Afterwards the dough pieces were moulded and shaped and proofed for 100 minutes at 34° C. at relative humidity of 90%. The fully proofed dough pieces were incised and baked in an oven at 240° C. for 30 minutes with initial steam addition.

Cell-free supernatants (with at least 2 mg/ml total Bradford protein) containing L01, L02, L03 or L04, respectively, were added to the flour at dosages ranging from 0.1 to maximal 4 ppm Bradford protein (1 ppm of Bradford protein is equal to 1 mg Bradford protein per kg of flour). As an additional control, the cell-free supernatant of the A. niger host strain devoid of L01-L04, containing 0.3 mg/ml Bradford protein, was tested dosing a volume (ml) equivalent to the highest volume of cell-free supernatant added to achieve the highest dosages of L01-L04 tested.

The various effects of the lipolytic enzymes at different dosages, both on dough and the final baked product, were compared to a blank, a loaf containing no extra additions, and a loaf containing 0.3% DATEM (Panodan® 80CP).

After cooling down to room temperature the volumes of the loaves were determined by an automated bread volume analyser (BVM-3, TexVol Instruments). The loaf volume of the blank bread is defined as 100%. Further effects were evaluated manually and visually by an experienced baker as follows:

Dough stability was addressed by visual judging the height/width ratio of a cross section of the bread on a scale of 1 to 5.
1=very flat (height/width ratio of cross section close to 0, 5=very high (height/width ratio of cross section of bread close to 0.8.)
Dough extensibility was addressed by manual judging on a scale of 1-5.
1=Very short to 5=very extensible
Oven spring: 1=incision closed completely to 5=completely open incision; teared
Crumb structure: 1=open/irregular crumb structure with thicker cell walls to 5=very fine/uniform crumb structure with thinner cell walls
Crumb colour: 1=very dark to 5=very bright white The results are given in Tables 7-11.

TABLE 7

Cell-free supernatant of the A. niger host strain (control) in comparison to the control and DATEM

|  | Blank | Control | DATEM |
|---|---|---|---|
| Volume (%) | 100 | 101 | 116 |
| Dough extensibility | 3 | 3 | 3 |
| Dough stability | 2 | 2 | 3 |
| Oven spring | 2 | 2 | 4 |
| Crumb structure | 2 | 2 | 4 |
| Crumb colour | 2 | 2 | 4 |

Cell-free supernatant of the A. niger host strain (control), dosed as described above, showed neither a positive, nor a negative effect on the baking performance compared to the blank.

TABLE 8

Baking performance of the lipolytic enzyme L01 at different dosages (mg total protein per kg flour (determined according to Bradford))

|  | Blank | 0.1 | 0.25 | 0.5 | 1 | 2 | 4 | DATEM |
|---|---|---|---|---|---|---|---|---|
| Volume (%) | 100 | 104 | 113 | 117 | 117 | 115 | 107 | 116 |
| Dough extensibility | 3 | 3 | 3 | 4 | 4 | 4 | 4 | 3 |
| Dough stability | 2 | 3 | 4 | 5 | 5 | 5 | 3 | 3 |
| Oven spring | 2 | 3 | 5 | 5 | 5 | 5 | 3 | 4 |
| Crumb structure | 2 | 2 | 3 | 4 | 5 | 4 | 4 | 4 |

TABLE 8-continued

Baking performance of the lipolytic enzyme L01 at different dosages (mg total protein per kg flour (determined according to Bradford))

| | Blank | 0.1 | 0.25 | 0.5 | 1 | 2 | 4 | DATEM |
|---|---|---|---|---|---|---|---|---|
| Crumb colour | 2 | 2 | 3 | 3 | 4 | 4 | 4 | 4 |

TABLE 9

Baking performance of the lipolytic enzyme L02 at different dosages (mg total protein per kg flour (determined according to Bradford))

| | Blank (0) | 0.1 | 0.25 | 0.5 | 1.0 | 2 | 4 | DATEM |
|---|---|---|---|---|---|---|---|---|
| Volume (%) | 100 | 97 | 112 | 114 | 114 | 115 | 110 | 116 |
| Dough extensibility | 3 | 3 | 3 | 3 | 4 | 4 | 4 | 3 |
| Dough stability | 2 | 3 | 4 | 4 | 5 | 5 | 3 | 3 |
| Oven spring | 2 | 2 | 3 | 4 | 5 | 5 | 3 | 4 |
| Crumb structure | 2 | 2 | 4 | 5 | 5 | 5 | 4 | 4 |
| Crumb colour | 2 | 2 | 3 | 3 | 4 | 4 | 4 | 4 |

TABLE 10

Baking performance of the lipolytic enzyme L03 at different dosages (mg total protein per kg flour (determined according to Bradford))

| | Blank (0) | 0.1 | 0.25 | 0.5 | 1.0 | 2 | DATEM |
|---|---|---|---|---|---|---|---|
| Volume (%) | 100 | 101 | 113 | 117 | 113 | 111 | 116 |
| Dough extensibility | 3 | 3 | 3 | 3 | 3 | 5 | 3 |
| Dough stability | 2 | 2 | 3 | 4 | 4 | 2 | 3 |
| Oven spring | 2 | 2 | 3 | 5 | 5 | 3 | 4 |
| Crumb structure | 2 | 2 | 3 | 5 | 3 | 3 | 4 |
| Crumb colour | 2 | 2 | 3 | 5 | 4 | 3 | 4 |

TABLE 11

Baking performance of the lipolytic enzyme L04 at different dosages (mg total protein per kg flour (determined according to Bradford))

| | Blank (0) | 0.1 | 0.25 | 0.5 | 1 | 2 | 4 | DATEM |
|---|---|---|---|---|---|---|---|---|
| Volume (%) | 100 | 110 | 117 | 116 | 116 | 116 | 112 | 116 |
| Dough extensibility | 3 | 3 | 3 | 3 | 3 | 3 | 4 | 3 |
| Dough stability | 2 | 3 | 5 | 4 | 4 | 5 | 3 | 3 |
| Oven spring | 2 | 4 | 5 | 5 | 5 | 4 | 3 | 4 |
| Crumb structure | 2 | 3 | 3 | 4 | 5 | 5 | 5 | 4 |
| Crumb colour | 2 | 2 | 4 | 3 | 4 | 5 | 4 | 4 |

Lipases L01 to L04 clearly improved dough stability, enhanced loaf volume, improved oven spring and improved crumb regularity compared to the blank. L01 to L04 were effective in replacing 0.3% DATEM, the effective dosage range being at least: 0.25-2.0 ppm for L01, L02 and L04, and 0.25-1 ppm for L03.

The lipases L01 to L04 did not influence the dough stickiness compared to the blank or the DATEM control. At higher dosages of L01 to L04 the doughs became slightly more extensible with no significant effect on the dough handling.

Example 6

Determination of Lipid Conversions in Dough of Mini-batard

Baking Experiment—Mini-batard

Mini-batards were baked from 150 gram dough pieces obtained by mixing 200 g flour (Kolibri™), 4.6 g compressed yeast, 4 g salt, 68 ppm ascorbic acid, 1 ppm Bakezyme® P500 (fungal alpha-amylase), 5 ppm Bakezyme® HSP6000 (fungal hemicellulase), and in total 57% water (flour weight set as 100%). Cell-free supernatants (with at least 2 mg/mL total protein) containing L01, L02, L03 or L04, respectively, were added at 0.5, 1.0 and 2.5 ppm Bradford protein. As an additional control, the cell-free culture supernatant of the A. niger host strain devoid of L01 to L04, containing 0.3 mg/ml Bradford protein, was tested at 3 ppm Bradford protein.

After mixing for 6 minutes and 15 seconds in a pin mixer, the dough was divided into two pieces of 150 g, rounded and proofed for 25 minutes at ambient temperature and relative humidity of 90%. The dough pieces were then moulded and shaped and proofed for 100 minutes at 32° C. and 85% relative humidity. The fully proofed dough pieces were incised and baked in an oven at 240° C. for 20 minutes with initial steam addition.

The baking results of the mini-batards baking experiments are comparable to those obtained at full scale, as described in Example 5.

Polar Lipids

Lipids were extracted by vigorously shaking freeze-dried and grinded fully proofed dough (see baking experiment mini-batard above) with water-saturated butanol. After centrifugation the clear supernatant is analysed on HPLC on LiChrospher 100 DIOL 5 μm (250×4.0 mm), lipoidic components were detected by Evaporative Light Scattering (Alltech ELSD 2000ES), at nitrogen flow of 1.5 l/min, temperature of 80° C., impactor on. Elution was performed using two mobile phases in a gradient program, at a flow of 1.0 ml/min:
A: heptane/isopropanol/butanol/tetrahydrofuran/iso-octan/water (64.5/17.5/7/5/5/1)
B: isopropanol/butanol/tetrahydrofuran/iso-octan/water (73/7/5/5/10).

To both elution solutions 77 μl ammoniac solution and 77 μl trifluor acetic acid is added per liter.
Gradient program: linear from 100% A to 100% B in 25 min, then 100% B for 5 min, then linear gradient from 100% B to 100% A for 0.5 min, and finally 100% A for 5 min with an injection volume of 20 μl and at a column temperature of 80° C.

References of galactolipids, phospholipids, for example monogalactosyldiglyceride, monogalactosylmonoglyceride, digalactosyldiglyceride, digalactosylmonoglyceride, phosphatidylcholine and lyso-phosphatidylcholine, were used to indicate the elution order of the various compounds and calculate their response factors and amounts present in the dough.

The dough lipid composition varies among the types of the harvests of the flour. Although one flour type was used for all experiments (Kolibry) data presented in Table 12 were obtained using flour from a different harvest than data presented in Tables 13-16.

The amounts of the main polar lipids in fully proofed dough containing the *A. niger* host strain background control sample (Table 12) or containing various amounts of L01 to L04 (Table 13-16), respectively, are presented in comparison to the respective lipid amounts of the blank dough. The results depicted in Table 12 clearly show that cell-free culture supernatant of the *A. niger* host strain (control) did not have any significant influence on the polar dough lipid composition compared to the blank at the high dosage tested.

From the results depicted in Tables 13-16 it can be unambiguously concluded that L01 to L04 efficiently convert galactosyldiglycerides to galactosylmonoglycerides, already at the lowest dosage tested, with a preference for digalactosyldiglyceride in comparison to monogalactosyldiglyceride, and also in comparison to phosphatidylcholine.

It is furthermore clear that, the high galactosylmonoglyceride level in the dough at a dosage of 0.5-2.5 ppm (Bradford protein) for L01 to L04 correlates to the baking performance described in Example 5.

TABLE 12

Polar lipids in fully proofed dough (expressed as g per kg freeze-dried dough) with the cell-free supernatant of the *A. niger* host strain (control) or without any addition (blank)

| Protein dosage [ppm] | MGDG | MGMG | DGDG | DGMG | PC | LPC |
|---|---|---|---|---|---|---|
| 0 (Blank) | 1.22 | 0.09 | 0.85 | 0.14 | 0.52 | 0.34 |
| 3 (Control) | 1.19 | 0.12 | 0.85 | 0.10 | 0.55 | 0.36 |

MGDG = monogalactosyldiglyceride;
MGMG = monogalactosylmonoglyceride;
DGDG = digalactosyldiglyceride;
DGMG = digalactosylmonoglyceride;
PC = phosphatidylcholine;
LPC = lyso-phosphatidylcholine

TABLE 13

Polar lipids in fully proofed dough (expressed as g per kg freeze-dried dough) containing various amounts of L01 (expressed as mg Bradford-protein per kg flour).

| L01 dosage [ppm] | MGDG | MGMG | DGDG | DGMG | PC | LPC |
|---|---|---|---|---|---|---|
| 0 (Blank) | 1.69 | 0.41 | 1.15 | 0.16 | 0.47 | 1.30 |
| 0.5 | 0.53 | 1.16 | 0.60 | 0.79 | 0.24 | 1.29 |
| 1.0 | 0.46 | 1.04 | 0.32 | 0.85 | 0.19 | 1.08 |
| 2.5 | 0.54 | 0.91 | 0.16 | 0.99 | 0.14 | 1.07 |

MGDG = monogalactosyldiglyceride;
MGMG = monogalactosylmonoglyceride;
DGDG = digalactosyldiglyceride;
DGMG = digalactosylmonoglyceride;
PC = phosphatidylcholine;
LPC = lyso-phosphatidylcholine

TABLE 14

Polar lipids in fully proofed dough (expressed as g per kg freeze-dried dough) containing various amounts of L02 (expressed as mg Bradford-protein per kg flour).

| L02 dosage [ppm] | MGDG | MGMG | DGDG | DGMG | PC | LPC |
|---|---|---|---|---|---|---|
| 0 (Blank) | 1.69 | 0.41 | 1.15 | 0.16 | 0.47 | 1.3 |
| 0.5 | 0.57 | 1.15 | 0.62 | 0.75 | 0.24 | 1.34 |
| 1.0 | 0.52 | 1.09 | 0.39 | 0.87 | 0.20 | 1.27 |
| 2.5 | 0.54 | 0.93 | 0.19 | 0.96 | 0.19 | 1.13 |

MGDG = monogalactosyldiglyceride;
MGMG = monogalactosylmonoglyceride;
DGDG = digalactosyldiglyceride;
DGMG = digalactosylmonoglyceride;
PC = phosphatidylcholine;
LPC = lyso-phosphatidylcholine

TABLE 15

Polar lipids in fully proofed dough (expressed as g per kg freeze-dried dough) containing various amounts of L03 (expressed as mg Bradford-protein per kg flour).

| L03 dosage [ppm] | MGDG | MGMG | DGDG | DGMG | PC | LPC |
|---|---|---|---|---|---|---|
| 0 (Blank) | 1.69 | 0.41 | 1.15 | 0.16 | 0.47 | 1.3 |
| 0.5 | 0.64 | 1.14 | 0.66 | 0.73 | 0.26 | 1.27 |
| 1.0 | 0.52 | 1.10 | 0.36 | 0.87 | 0.21 | 1.23 |
| 2.5 | 0.51 | 0.94 | 0.16 | 0.95 | 0.20 | 1.11 |

MGDG = monogalactosyldiglyceride;
MGMG = monogalactosylmonoglyceride;
DGDG = digalactosyldiglyceride;
DGMG = digalactosylmonoglyceride;
PC = phosphatidylcholine;
LPC = lyso-phosphatidylcholine

TABLE 16

Polar lipids in fully proofed dough (expressed as g per kg freeze-dried dough) containing various amounts of L04 (expressed as mg Bradford-protein per kg flour).

| L04 dosage [ppm] | MGDG | MGMG | DGDG | DGMG | PC | LPC |
|---|---|---|---|---|---|---|
| 0 (Blank) | 1.69 | 0.41 | 1.15 | 0.16 | 0.47 | 1.3 |
| 0.5 | 0.69 | 1.05 | 0.78 | 0.61 | 0.31 | 1.22 |
| 1.0 | 0.49 | 1.08 | 0.40 | 0.83 | 0.21 | 1.17 |
| 2.5 | 0.52 | 0.95 | 0.18 | 0.93 | 0.21 | 1.11 |

MGDG = monogalactosyldiglyceride;
MGMG = monogalactosylmonoglyceride;
DGDG = digalactosyldiglyceride;
DGMG = digalactosylmonoglyceride;
PC = phosphatidylcholine;
LPC = lyso-phosphatidylcholine Apolar Lipids Apolar lipids are extracted by vigorously shaking freeze-dried and grinded fully proofed dough (see Baking experiment-mini batard above) with heptane containing 1% acetic acid. After centrifugation the clear supernatant is analysed on HPLC on Spherisorb S3CN (Phenomenex 00D-0097-EO; 100×4.6 mm), lipoidic components are detected by Evaporative Light Scattering (Alltech ELSD 2000ES), at nitrogen flow of 1.5 l/min, temperature of 40° C., impactor off. Elution is performed using two mobile phases (A: heptane and B: tert-butyl-methyl ether containing 1% acetic acid) in the following linear gradient program, at a flow of 1.0 ml/min, injection volume 20 μl and ambient column temperature:

| Time (min) | A (%) | B (%) |
|---|---|---|
| 0 | 98 | 2 |
| 3 | 98 | 2 |
| 15 | 80 | 20 |
| 27 | 0 | 100 |
| 32 | 0 | 100 |
| 32.1 | 98 | 2 |
| 40 | 98 | 2 |

References of tri-, di-, monoglycerides and fatty acid are used to indicate the elution order of the various compounds and calculate their response factors and amounts present in the dough.

Example 7

Baking Experiment

Partial DATEM Replacement in Full Scale Batard

For some baking applications, it can be beneficial to partially replace DATEM by the lipolytic enzyme according to the invention, rather than to completely replace DATEM, as described in Example 5. In this example the effect of compositions comprising DATEM and L01 and of compositions comprising DATEM and L02 on properties of the dough and of the baked product was analysed.

In order to assess the amount of lipolytic enzyme necessary to replace half of the DATEM in a recipe with 0.3% DATEM, the baking performance in full scale batard of combinations of 0.15% DATEM with various amounts of cell-free supernatants with at least 2 mg/ml total Bradford protein, containing L01 or L02, respectively, were studied.

The various effects of the lipolytic enzymes at different dosages combined with 0.15% DATEM, both on dough and the final baked product, were compared to a blank, i.e. a loaf containing neither DATEM nor the lipolytic enzyme, and to loaves containing a total DATEM concentration of 0.15% or 0.3%, respectively, or to loaves containing 0.25 ppm L01 or L02.

The composition comprising DATEM (Lametop 501) and L01 was tested using the following full scale batard recipe and process: 2000 g of flour (i.e. 1800 g Kolibri™ and 200 g Ibis™) 47 g compressed yeast, 40 g salt, 88 ppm ascorbic acid, 3 ppm Bakezyme® P500 (fungal alpha-amylase), 15 ppm Bakezyme® HSP6000 (fungal hemicellulase) and 57% water was mixed in a Diosna mixer for 2 minutes at speed 1 and 71 Wh at speed 2, to a final dough temperature of 27° C. The dough was divided in 6 pieces of 350 g, rounded and proofed for 20 minutes at 32° C. and 90% relative humidity. Afterwards the dough pieces were moulded and shaped and proofed for 90 minutes at 34° C. at relative humidity of 90%. The fully proofed dough pieces were incised and baked in an oven at 240° C. for 30 minutes with initial steam addition. The flour batches used in this trial originated from a different harvest compared to the flour batches used in Examples 5 and 6. The higher ascorbic acid concentration in this trial was used following the instruction of the supplier for this batch of Kolibri flour.

The composition comprising DATEM (Lametop) and L02 was tested using the following full scale batard recipe and process:

2000 g of flour (i.e. 1800 g Kolibri™ and 200 g Ibis™), 47 g compressed yeast, 40 g salt, 68 ppm ascorbic acid, 2 ppm Bakezyme® P500 (fungal alpha-amylase), 15 ppm Bakezyme® HSP6000 (fungal hemicellulase) and 57% water was mixed in a Diosna mixer for 2 minutes at speed 1 and 71 Wh at speed 2, to a final dough temperature of 27° C. The dough was divided in 6 pieces of 350 g, rounded and proofed for 20 minutes at 32° C. and 90% relative humidity. Afterwards the dough pieces were moulded and shaped and proofed for 100 minutes at 34° C. at relative humidity of 90%. The fully proofed dough pieces were incised and baked in an oven at 240° C. for 30 minutes with initial steam addition. Again, the flour batch used in this trial originated from a different harvest compared to the flour batches used for the composition comprising L01 and to the flour batches used in Examples 5 and 6.

The results of the compositions comprising DATEM and L01 are given in Table 17, while the results of the compositions comprising DATEM and L02 are given in Table 18. Bread and dough characteristics were evaluated as described in Example 5.

TABLE 17

Baking performance of compositions of the lipolytic enzyme L01 (given as ppm, i.e. mg total protein per kg flour (determined according to Bradford)) and DATEM (given as %, i.e. g DATEM per 100 g flour)

| L01 [ppm] | 0 | 0 | 0.04 | 0.08 | 0.12 | 0 | 0.25 |
|---|---|---|---|---|---|---|---|
| DATEM (%) | 0 | 0.15 | 0.15 | 0.15 | 0.15 | 0.3 | 0 |
| Volume (%) | 100 | 113 | 124 | 123 | 121 | 120 | 121 |
| Dough extensibility | 3 | 3 | 4 | 4 | 4 | 4 | 4 |
| Dough stability | 1 | 2 | 2 | 4 | 5 | 4 | 4 |
| Oven spring | 1 | 2 | 2 | 4 | 5 | 3 | 4 |
| Crumb structure | 1 | 2 | 3 | 4 | 5 | 4 | 4 |
| Crumb colour | 2 | 2 | 3 | 4 | 5 | 4 | 4 |

TABLE 18

Baking performance of compositions of the lipolytic enzyme L02 (ppm, i.e. mg total protein per kg flour (determined according to Bradford)) and DATEM (given as %, i.e. g DATEM per 100 g flour)

| L02 [ppm] | 0 | 0 | 0.04 | 0.07 | 0.10 | 0 | 0.25 |
|---|---|---|---|---|---|---|---|
| DATEM (%) | 0 | 0.15 | 0.15 | 0.15 | 0.15 | 0.3 | 0 |
| Volume (%) | 100 | 118 | 125 | 123 | 130 | 127 | 124 |
| Dough extensibility | 3 | 3 | 4 | 4 | 4 | 3 | 4 |
| Dough stability | 1 | 2 | 2 | 4 | 5 | 3 | 4 |
| Oven spring | 1 | 2 | 3 | 4 | 5 | 4 | 4 |
| Crumb structure | 1 | 2 | 3 | 4 | 5 | 4 | 4 |
| Crumb colour | 2 | 2 | 3 | 4 | 5 | 4 | 4 |

These results clearly show, that a composition comprising 0.15% DATEM and 0.08 ppm L01 or 0.07 ppm L02, respectively, was effective in replacing 0.3% DATEM, leading to comparable dough stability, loaf volume, oven spring, crumb structure and crumb colour. A minimal dosage of 0.25 ppm L01 or L02, respectively, can be sufficient to replace 0.3% DATEM, as also shown in Example 5. Surprisingly, a combination of approximately half the L01 dosage (0.12 ppm) or half the L02 dosage (0.10 ppm), respectively, with half the DATEM dosage (0.15% DATEM) showed an improvement of dough stability, crumb structure and oven spring compared to 0.3% DATEM alone and compared to 0.25 ppm L01 alone or 0.25 ppm L02 alone, respectively. This indicates that compositions comprising DATEM and lipolytic enzymes L01 or L02 according to the invention show a synergistic effect.

Example 8

Effect of a Lipolytic Enzyme of the Invention in Victoria Cake

Lipolytic enzymes can be used in cake recipes to improve e.g. the emulsion stability of the batter. Here, L01 was tested for its effect in Victoria cake.

Victoria cakes were prepared using a Hobart mixer provided with a flat beater mixer, as follows:
1. mix unsalted butter, 19%, and sugar, 21%
2. add dry ingredients:

heat-treated cake flour (Albatros, Meneba), 30%; baking powder (SAPP 15), 0.4%; sodium bicarbonate, 0.3%; milk powder, 0.4%; salt, 0.13% and L01, as indicated in table 19 and mix 3. add liquid ingredients during mixing:
   whole egg, 23% (w/w), water, 3.6% (w/w), 19% (w/w), glycerine, 2.1% (w/w),
4. scrape bowl and mix at highest speed for 2 minutes Percentages of the ingredients are given in % (w/w) final batter weight. Dosages of L01 are given in ppm, i.e. Bradford protein (mg) relative to the mass of the whole liquid egg (kg) in the blank recipe.

Batters, final batter weight 1496 g, were scaled to 300 gram batter weight per pan (diameter 13 cm) and baked at 165/170° C. for 45 min.

The various effects of L01, both on the batter and the final cake, were compared to a blank, i.e. a batter/cake not containing the lipolytic enzyme L01.

Specific batter density, i.e. batter weight per batter volume (g/l), was measured by determining the weight of a defined batter volume (here 300 ml).

The volumes of the cakes were determined by an automated bread volume analyser (BVM-3, TexVol Instruments), the cake weighted and the specific cake volume (ml/g) calculated. The specific cake volume of the blank cake was defined as 100%.

Cakes were stored one by one in polythene bags at room temperature. One, 8 and 18 days after baking, crumb firmness and resilience were measured using a SMS TAX2 texture analyser (Stable Microsystems), using a 4 cm cylindrical probe. Per cake, four slices, taken from the centre of the cake, were measured. The probe was pushed 10 mm into a slice of cake and the resistance recorded directly and after 30 seconds. The relative values (percentage decrease) represent resilience, the ability of the product to cope with stress. The absolute value at t=0 represents firmness.

Crumb pore homogeneity was evaluated visually by an experienced baker on a relative scale of 1 to 10:1=heterogeneous, irregular crumb structure to 10=homogeneous, uniform crumb structure.

Crumb pore diameter was evaluated visually by an experienced baker on a relative scale of 1 to 10:1=very large (open crumb structure) to 10=very small (very fine crumb structure).

TABLE 19

Performance of lipolytic enzyme L01 in Victoria cake

|  | days after baking |  |  |
| --- | --- | --- | --- |
| L01 [ppm (mg protein/kg whole liquid egg)] |  | 0 | 3.29 |
| Specific batter density [g/l] |  | 963 | 940 |
| Cake specific volume [%] | 1 | 100 | 110 |
| Crumb pore homogeneity | 1 | 5 | 8 |
| Crumb pore diameter | 1 | 5 | 8 |
| Crumb firmness | 1 | 1247 | 907 |
|  | 8 | 1703 | 1223 |
|  | 18 | 2324 | 1556 |
| Crumb elasticity | 1 | 47 | 46 |
|  | 8 | 43 | 43 |
|  | 18 | 42 | 41 |

Addition of L01 resulted in decreased batter density, increased cake volume, more homogeneous crumb with smaller pores and reduced crumb firmness both initially and during shelf life relative to the blank cake. No significant differences in crumb resilience were observed for the cakes tested.

These results clearly show that lipolytic enzymes of the invention improved the emulsion stabilization of the cake batter, resulting in overall improved cake quality. These results also show that the lipolytic enzymes of the invention are not only functional in replacing emulsifiers such as for example DATEM or SSL/CSL in bread recipes, but also in emulsifier-free cake recipes, as addition of the lipolytic enzyme of the invention resulted in increased cake volume, an effect, that can be obtained by adding emulsifiers such as glycerol monostearate, and in increased cake softness, an effect that is usually obtained by adding emulsifiers such as monoglycerides.

Example 9

Effect of a Lipolytic Enzyme of the Invention on Batter and Crumb Properties in Egg-reduced Sponge Cake Egg reduction in sponge cake recipes results in a firm and crumbly cake with a poor, open, crumb structure. Lipolytic enzymes can be used to improve overall cake quality in such egg-reduced cake recipes. Here, the effect of L01 alone and in combination with phospholipase A in egg-reduced sponge cake was tested.

As phospholipase Cakezyme™ (DSM Food Specialties, The Netherlands) was used, a phospholipase A2 produced in *A. niger* containing 5000 CPU/g. Phospholipase activity was determined using rac 1,2-dioctanoyldithio phosphatidylcholine as substrate, the reaction was followed spectrophotometrically at 405 nm and the activity expressed in chromogenic phospholipase units: 1 CPU (Chromogenic Phospholipase Unit) was normalised to 1 EYU (Egg Yolk Unit), which is defined as the amount of enzyme that liberates 1 μmmol of acid per minute from egg yolk at 40° C. and pH 8.0.

Sponge cakes were prepared using a Hobart mixer provided with a wire whisk mixer, as follows:
  ingredients in % (w/w) final batter weight:
  sugar, 25%; heat-treated cake flour (Albatros, Meneba), 21%; baking powder (SAPP 28), 0.6%; wheat starch, 8.3%; emulsifier (BV40), 3.3%; sodium bicarbonate, 0.4%; whole egg (for full egg reference batter: 30%, for egg-reduced batter: 24%); water (for full egg reference batter: 11.4%, for egg-reduced batter: 17.4%)
1. mix all ingredients, including the respective amounts of L01 and/or phospholipase A, as indicated in the table 20, for 1 min speed 1
2. mix for 5 minutes at speed 3
3. mix for 1 minute at speed 1

Batters, final batter weight 848 g, were scaled to 400 g batter weight per pan (diameter 28 cm) and baked at 180/180° C. for 25 min.

Dosages of L01 are given in ppm i.e. Bradford protein (mg) relative to the mass of the whole liquid egg (kg) in the full egg reference batter, dosages of phospholipase A in % Cakezyme™ (product) weight relative to the mass of whole liquid egg in the full egg reference batter.

Cake crumb structure was evaluated visually by an experienced baker on a relative scale of 1 to 10:1=open/irregular crumb structure with thicker cell walls to 10=very fine/uniform crumb structure with thinner cell walls Here crumb softness was judged visually with relative scores 1: very firm to 10: very soft.

Crumb cohesiveness was judged manually with relative scores 1: very crumbly to 10: cohesive.

TABLE 20

Performance of lipolytic enzyme L01, phospholipase A and a combination thereof in egg-reduced sponge cake in comparison to full-egg sponge cake

|  | Full egg reference | | Egg-reduced* | | |
|---|---|---|---|---|---|
| L01 [ppm (mg protein/ kg whole liquid egg)] | 0 | 0 | 0.23 | 0 | 0.23 |
| phospholipase A [% w Cakezyme/w eggs] | 0 | 0 | 0 | 0.04 | 0.04 |
| crumb structure | 5 | 3 | 7 | 6 | 9 |
| crumb softness (4 days after baking) | 6 | 3 | 5 | 7 | 10 |
| crumb cohesiveness | 9 | 5 | 8 | 7 | 9 |

*20% less whole eggs than for full egg reference

Reduction of eggs by 20% and compensation of the corresponding batter weight by water resulted in decreased batter viscosity, decreased crumb softness, poorer crumb structure and decreased crumb cohesiveness compared to the full egg reference.

By adding phospholipase A to egg-reduced batter, batter viscosity was restored to the level of the full egg batter, crumb softness and cohesiveness was considerably improved compared to the egg-reduced cake, and crumb structure was even slightly improved compared to the full egg cake.

Adding L01 to egg-reduced batter resulted in slightly improved batter viscosity and finer crumb structure compared to the full egg reference, and in improved crumb softness and, especially, improved crumb cohesiveness compared to the egg-reduced reference.

Surprisingly, adding a composition comprising L01 and phospholipase A to egg-reduced cake batter even further improved the batter viscosity, crumb structure and crumb softness in comparison to the full egg and the egg-reduced recipes in which either L01 or phospholipase A were added, and restored crumb cohesiveness to the level of full egg cake.

From these results it is clear that addition of a lipolytic enzyme of the invention alone or in comination with phospholipase A improves the overall properties of egg-reduced cake. In an egg-reduced cake recipe, even a better crumb softness and structure than in full egg cake can be achieved when a lipolytic enzyme of the invention is added alone and especially in combination with phospholipase A.

Example 10

The Effect of a Lipolytic Enzyme of the Invention on the Crispiness of a Laminated Dough Laminated dough was made from 1000 g Edelweiss flour, 430 g water, 100 g egg, 50 g yeast, 20 g salt, 10 g sugar, 15 g bread improver and L01. L01 was dosed at 0.23 ppm, i.e. mg protein, determined according to Bradford, per kg flour. The reference had no enzyme. After appropriate resting the dough was rolled out into a layer. A layer of laminating margarine (Trio Korst, Unipro, Bergen op Zoom, the Netherlands) was folded into the dough sheet. This then was rolled out into a laminated dough in a standard procedure. Ribbons were cut from the final dough and folded into butterfly-shaped pastries and baked in the oven at 235° C. for 20 minutes. The products were tested after two days storage in a semi-closed cabinet.

Mechanical testing was performed using a texture analyzer (TA-XT Plus, Stable Micro systems Ltd., Surrey, UK). At least 10 pastries of the reference and the product with L01 added were characterised using a 25 mm wedge probe at a speed of 1 mm/sec after 2 days of storage.

The force versus distance compression curve was analyzed and parameters were obtained from the compression curve using a macro from the Texture Analysis Software. From StatGraphics (statistical analysis and modeling software) a scatter plot was obtained to determine the statistically significant differences between the reference pastries and pastries containing L01. The results of the compression experiments after 2 days of storage at ambient conditions are presented in Table 21. On five textural parameters significant differences were found between the reference and the products prepared with L01. The products with L01 were moreover found to be easier moulding than the reference.

TABLE 21

Crispiness characteristics in laminated baked products after 2 days of storage at ambient conditions.

|  | Reference | L01 |
|---|---|---|
| Distance (mm) | 14.3 ± 1.6 | 6.5 ± 1.1 |
| First peak force (g) | 1390 ± 273 | 1273 ± 945 |
| Slope (g/s) | 159 ± 67 | 998 ± 498 |
| Highest peak force (g) | 1419 ± 285 | 4207 ± 1207 |
| Area (g * s) | 1416 ± 3165 | 23908 ± 8214 |
| Number of fraction events | 0 | 9 ± 5 |

This shows that laminated baked products prepared with a lipolytic enzyme according to the invention are crispier after two days of storage at ambient conditions than products prepared without enzyme.

The invention claimed is:

1. An isolated polypeptide having lipolitic activity comprising:
   (a) amino acids 34 to 304 of SEQ ID NO: 2; or
   (b) an amino acid sequence at least 90% identical to amino acids 34 to 304 of SEQ ID NO: 2.

2. An isolated polypeptide according to claim 1 comprising:
   amino acids 34 to 304 of SEQ ID NO: 4, or
   amino acids 34 to 304 of SEQ ID NO: 6, or
   amino acids 34 to 304 of SEQ ID NO: 8.

3. An isolated polypeptide according to claim 1 obtained by expressing a polynucleotide encoding said isolated polypeptide.

4. The isolated polypeptide of claim 1, wherein said polypeptide consists of an amino acid sequence selected from the group consisting of:
   amino acid residues 34-304 of SEQ ID NO: 2;
   amino acid residues 34-303 of SEQ ID NO: 2;
   amino acid residues 31-304 of SEQ ID NO: 2;
   amino acid residues 31-303 of SEQ ID NO: 2;
   amino acid residues 34-307 of SEQ ID NO: 2;
   amino acid residues 34-302 of SEQ ID NO: 2; and
   amino acid residues 31-307 of SEQ ID NO: 2.

5. A method for manufacturing a polypeptide according to claim 1 comprising cultivating a recombinant host cell under conditions which allow for expression of a polynucleotide encoding the polypeptide according to claim 1 and optionally recovering the encoded polypeptide from the cell or culture medium.

6. Baking enzyme composition comprising an isolated polypeptide having lipolytic activity according to claim 1 and one or more additional enzymes.

7. A baking enzyme composition according to claim 6, wherein the additional enzyme is selected from the group consisting of an amylase, an alpha-amylase, a beta-amylase, a maltogenic amylase, a non-maltogenic amylase, a cyclodextrin, a glucotransferase, a protease, a peptidase, an exopeptidase, a transglutaminase, a lipase, a galactolipase, a phospholipase, phospholipase A, a cellulase, a hemicellulase, a xylanase, a protein disulfide isomerase, a glycosyltransferase, a peroxidase, a laccase, an oxidase, a hexose oxidase, a glucose oxidase, an aldose oxidase, a pyranose oxidase, a lipoxygenase, and an L-amino acid oxidase.

8. Baking composition comprising diacetyl tartaric acid esters of mono- and diglycerides (DATEM) and an isolated polypeptide having lipolytic activity according to claim 1.

9. A dough comprising the polypeptide according to claim 1.

10. Method to prepare a dough comprising the step of adding the polypeptide according to claim 1 to at least one dough ingredient.

11. Method to prepare a baked product comprising the step of baking the dough according to claim 9.

12. A method to prepare a baked product comprising the step of baking a batter comprising the polypeptide of claim 1.

13. A method of producing a cake comprising adding the polypeptide of claim 1 to at least one cake ingredient.

14. A method for preparing a dairy product wherein an isolated polypeptide according to claim 1, is added to a dairy composition used in the production of a dairy product under conditions sufficient for the enzyme to react.

15. An isolated nucleic acid encoding a polypeptide according to claim 1.

16. The isolated nucleic acid of claim 15, wherein the isolated nucleic acid comprises:
   (a) SEQ ID NO: 1; or
   (b) a nucleotide sequence at least 90% identical to SEQ ID NO: 1; or
   (c) a sequence which is degenerate as a result of the degeneracy of the genetic code to a sequence as defined in any one of (a) or (b); or
   (d) a complement of a nucleotide sequence according to one of (a)-(c); or
   (e) a nucleotide sequence which hybridises under high stringency conditions with a complement of SEQ ID NO: 1, wherein the stringent conditions are hybridizing the isolated nucleic acid with the complement of SEQ ID NO: 1 at 68° C. in 5×SCC/5×Denhardt's solution/1.0% sodium dodecyl sulfate (SDS) and washing the isolated nucleic acid hybridized to the complement of SEQ ID NO: 1 in 0.2×SCC/0.1% SDS at room temperature.

17. An isolated polynucleotide according to claim 15 which is produced synthetically.

18. An isolated polynucleotide according to claim 15 having a nucleotide sequence according to SEQ ID NO: 3 or according to SEQ ID NO: 5 or according to SEQ ID NO: 7.

19. A vector comprising a polynucleotide sequence according to claim 15.

20. A vector according to claim 19 which is an expression vector wherein the polynucleotide sequence is operably linked with at least one regulatory sequence allowing for expression of the polynucleotide sequence in a suitable host cell.

21. A vector according to claim 20 wherein the suitable host cell is a filamentous fungus.

22. A recombinant host cell comprising a polynucleotide according to claim 15.

23. A recombinant host cell according to claim 22 capable of expressing or over-expressing said polynucleotide.

* * * * *

SEQUENCE LISTING

<160> NUMBER OF SEQ ID NOS: 8

<210> SEQ ID NO 1
<211> LENGTH: 1038
<212> TYPE: DNA
<213> ORGANISM: Artificial sequence
<220> FEATURE:
<223> OTHER INFORMATION: DNA L01 lipase gene

<400> SEQUENCE: 1
atgcttctcc tctccctcct ctccattgtc accctcgctg ttgcttctcc tctgtccgtt    60

```
gaggagtacg ccaaggccct cgaggagcgt gccgtcaccg tctcctcctc cgagctcaac      120
aacttcaagt tctacatcca gcacggtgct gctgcctact gcaactccga gactgctgct      180
ggtgccaacg tcacctgcac tggcaacgcc tgccccgaga ttgaggccaa cggtgtcacc      240
gttgttgcct ccttcactgg taccaagact ggtatcggtg gctacgtctc caccgacaac      300
accaacaagg agatcgtcct tctttccgt ggcagcatca acatccgcaa ctggctgacc       360
aacctggact tcggccagga tgactgctct ctgacctccg gctgcggtgt ccactccggt      420
ttccagcgtg cctgggagga gattgccgac aacctgaccg ctgctgttgc caaggccaag      480
actgccaacc ccgactacaa ggttgttgcc actggccact ccctgggtgg tgctgttgcc      540
accctggctg gtgccaacct ccgtgctgct ggtacccccc tcgacatcta cacctacggc      600
tctccccgtg tcggcaacgc cgagcttgct gagttcatct ccaaccagac tggtggtgag      660
ttccgtgtca cccacggtga tgaccccgtc cccgtcttc ctcctctgat cttcggctac       720
cgccacacct cccccgagta ctggctcgat ggcagcggtg gtgacaagat caactacacc      780
atcaacgaca tcaaggtctg cgagggtgct gccaacctgc agtgcaacgg tggtaccctg      840
ggtctcgaca ttgctgctca cctgcactac ttccaggcca ctgatgcctg caacgccggt      900
ggtttcagct ggcgccgcta ccgctctgct gagagcgttg acaagcgtgc caccatgact      960
gatgctgagc tcgagaagaa gctcaacagc tacgtgcaga tggacaagga gtacgtcaag     1020
aacaaccagg ctcgctcc                                                    1038

<210> SEQ ID NO 2
<211> LENGTH: 346
<212> TYPE: PRT
<213> ORGANISM: Artificial sequence
<220> FEATURE:
<223> OTHER INFORMATION: L01 lipase protein

<400> SEQUENCE: 2

Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
            20                  25                  30

Thr Val Ser Ser Ser Glu Leu Asn Asn Phe Lys Phe Tyr Ile Gln His
        35                  40                  45

Gly Ala Ala Ala Tyr Cys Asn Ser Glu Thr Ala Ala Gly Ala Asn Val
    50                  55                  60

Thr Cys Thr Gly Asn Ala Cys Pro Glu Ile Glu Ala Asn Gly Val Thr
65                  70                  75                  80

Val Val Ala Ser Phe Thr Gly Thr Lys Thr Gly Ile Gly Gly Tyr Val
                85                  90                  95

Ser Thr Asp Asn Thr Asn Lys Glu Ile Val Leu Ser Phe Arg Gly Ser
            100                 105                 110

Ile Asn Ile Arg Asn Trp Leu Thr Asn Leu Asp Phe Gly Gln Asp Asp
        115                 120                 125

Cys Ser Leu Thr Ser Gly Cys Gly Val His Ser Gly Phe Gln Arg Ala
    130                 135                 140

Trp Glu Glu Ile Ala Asp Asn Leu Thr Ala Ala Val Ala Lys Ala Lys
145                 150                 155                 160

Thr Ala Asn Pro Asp Tyr Lys Val Val Ala Thr Gly His Ser Leu Gly
                165                 170                 175

Gly Ala Val Ala Thr Leu Ala Gly Ala Asn Leu Arg Ala Ala Gly Thr
            180                 185                 190
```

```
Pro Leu Asp Ile Tyr Thr Tyr Gly Ser Pro Arg Val Gly Asn Ala Glu
        195                 200                 205
Leu Ala Glu Phe Ile Ser Asn Gln Thr Gly Gly Glu Phe Arg Val Thr
    210                 215                 220
His Gly Asp Asp Pro Val Pro Arg Leu Pro Leu Ile Phe Gly Tyr
225                 230                 235                 240
Arg His Thr Ser Pro Glu Tyr Trp Leu Asp Gly Ser Gly Gly Asp Lys
                245                 250                 255
Ile Asn Tyr Thr Ile Asn Asp Ile Lys Val Cys Glu Gly Ala Ala Asn
            260                 265                 270
Leu Gln Cys Asn Gly Gly Thr Leu Gly Leu Asp Ile Ala Ala His Leu
        275                 280                 285
His Tyr Phe Gln Ala Thr Asp Ala Cys Asn Ala Gly Gly Phe Ser Trp
    290                 295                 300
Arg Arg Tyr Arg Ser Ala Glu Ser Val Asp Lys Arg Ala Thr Met Thr
305                 310                 315                 320
Asp Ala Glu Leu Glu Lys Lys Leu Asn Ser Tyr Val Gln Met Asp Lys
                325                 330                 335
Glu Tyr Val Lys Asn Asn Gln Ala Arg Ser
            340                 345

<210> SEQ ID NO 3
<211> LENGTH: 1038
<212> TYPE: DNA
<213> ORGANISM: Artificial sequence
<220> FEATURE:
<223> OTHER INFORMATION: DNA L02 lipase gene

<400> SEQUENCE: 3
atgcttctcc tctccctcct ctccattgtc accctcgctg ttgcttctcc tctgtccgtt       60
gaggagtacg ccaaggccct cgaggagcgt gccgtcaccg tctcctcctc cgagctcaac      120
aacttcaagt tctacatcca gcacggtgct gctgcctact gcaactccga gactgctgct      180
ggtgccaagg tcacctgctc caacaacggc tgccccgagg ttgaggccaa cggtgtcacc      240
gttgttgcct ccttcgtcgg taccaagacc ggtatcggtg gctacgtggc caccgacaac      300
gcccgcaagg agatcgtcct ctccttccgt ggcagcatca acatccgcaa ctggctgacc      360
aacctggact tcggccagga ggactgctct ctgacctccg gctgcggtgt ccactccggt      420
ttccagcgtg cctgggagga gattgccgac aacttgactg ctgctgttgc caaggccaag      480
actgccaacc ccgactacaa ggtcgtcagc actggccact ctcttggtgg tgctgttgcc      540
accctggctg ctgccaacct ccgtgtcggt ggtactcctc ttgacatcta cacctacggc      600
tctccccgtg tcggcaacgc cgagctctcc gctttcgtct ccaaccagac tggtggtgag      660
ttccgtgtca cccacggtga tgaccccgtc ccccgtcttc ctcctctgat cttcggctac      720
cgccacacct cccccgagta ctggctcgat ggcagcggtg gtgacaaggt cgactacacc      780
atcaacgaca tcaaggtctg cgagggtgct gccaacctgc agtgcaacgg tggtaccctg      840
ggtctcgaca ttgctgctca cctgcactac ttccaggcca ctgatgcctg caacgccggt      900
ggtttcagct ggcgccgcta ccgctctgct gagagcgttg acaagcgtgc caccatgact      960
gatgctgagc tcgagaagaa gctcaacagc tacgtgcaga tggacaagga gtacgtcaag     1020
aacaaccagg ctcgctcc                                                    1038

<210> SEQ ID NO 4
<211> LENGTH: 346
```

<212> TYPE: PRT
<213> ORGANISM: Artificial sequence
<220> FEATURE:
<223> OTHER INFORMATION: L02 lipase protein

<400> SEQUENCE: 4

Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
            20                  25                  30

Thr Val Ser Ser Ser Glu Leu Asn Asn Phe Lys Phe Tyr Ile Gln His
        35                  40                  45

Gly Ala Ala Ala Tyr Cys Asn Ser Glu Thr Ala Ala Gly Ala Lys Val
    50                  55                  60

Thr Cys Ser Asn Asn Gly Cys Pro Glu Val Glu Ala Asn Gly Val Thr
65                  70                  75                  80

Val Val Ala Ser Phe Val Gly Thr Lys Thr Gly Ile Gly Gly Tyr Val
                85                  90                  95

Ala Thr Asp Asn Ala Arg Lys Glu Ile Val Leu Ser Phe Arg Gly Ser
            100                 105                 110

Ile Asn Ile Arg Asn Trp Leu Thr Asn Leu Asp Phe Gly Gln Glu Asp
        115                 120                 125

Cys Ser Leu Thr Ser Gly Cys Gly Val His Ser Gly Phe Gln Arg Ala
    130                 135                 140

Trp Glu Glu Ile Ala Asp Asn Leu Thr Ala Ala Val Ala Lys Ala Lys
145                 150                 155                 160

Thr Ala Asn Pro Asp Tyr Lys Val Val Ser Thr Gly His Ser Leu Gly
                165                 170                 175

Gly Ala Val Ala Thr Leu Ala Ala Ala Asn Leu Arg Val Gly Gly Thr
            180                 185                 190

Pro Leu Asp Ile Tyr Thr Tyr Gly Ser Pro Arg Val Gly Asn Ala Glu
        195                 200                 205

Leu Ser Ala Phe Val Ser Asn Gln Thr Gly Gly Glu Phe Arg Val Thr
    210                 215                 220

His Gly Asp Asp Pro Val Pro Arg Leu Pro Pro Leu Ile Phe Gly Tyr
225                 230                 235                 240

Arg His Thr Ser Pro Glu Tyr Trp Leu Asp Gly Ser Gly Gly Asp Lys
                245                 250                 255

Val Asp Tyr Thr Ile Asn Asp Ile Lys Val Cys Glu Gly Ala Ala Asn
            260                 265                 270

Leu Gln Cys Asn Gly Gly Thr Leu Gly Leu Asp Ile Ala Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
            340                 345

<210> SEQ ID NO 5
<211> LENGTH: 1038
<212> TYPE: DNA
<213> ORGANISM: Artificial sequence
<220> FEATURE:
<223> OTHER INFORMATION: DNA L03 lipase gene

<400> SEQUENCE: 5

```
atgcttctcc tctccctcct ctccattgtc accctcgctg ttgcttctcc tctgtccgtt      60
gaggagtacg ccaaggccct cgaggagcgt gccgtcaccg tctcctcctc cgagctcaac     120
aacttcaagt tctacatcca gcacggtgct gctgcctact gcaactccga gactgctgct     180
ggtgccaagg tcacctgctc tggcaacggc tgccccgagg ttgaggccaa cggtgtcacc     240
gttgttgcct ccttcaccgg taccaagacc ggtatcggtg gctacgtggc caccgacaac     300
gcccgcaagg agatcgtcct ctccttccgt ggcagcatca acatccgcaa ctggctgacc     360
aacctggact tcggccagga tgactgctct ctgacctccg gctgcggtgt ccactccggt     420
ttccagcgtg cctgggagga gattgccgac aacttgactg ctgctgttgc caaggccaag     480
actgccaacc ccgactacaa ggtcgtcgcc actggccact ccctgggtgg tgctgttgcc     540
accctggctg gtgccaacct ccgtgtcggt ggtactcctc ttgacatcta cacctacggc     600
tctccccgtg tcggcaacgc cgagcttgct gctttcgtct ccaaccagac tggtggtgag     660
ttccgtgtca cccacggtga tgaccccgtc cccgtcttc ctcctctgat cttcggctac     720
cgccacacct cccccgagta ctggctcgat ggcagcggtg tgacaagat cgactacacc     780
atcaacgaca tcaaggtctg cgagggtgct gccaacctgc agtgcaacgg tggtaccctg     840
ggtctcgaca ttgctgctca cctgcactac ttccaggcca ctgatgcctg caacgccggt     900
ggtttcagct ggcgccgcta ccgctctgct gagagcgttg acaagcgtgc caccatgact     960
gatgctgagc tcgagaagaa gctcaacagc tacgtgcaga tggacaagga gtacgtcaag    1020
aacaaccagg ctcgctcc                                                    1038
```

<210> SEQ ID NO 6
<211> LENGTH: 346
<212> TYPE: PRT
<213> ORGANISM: Artificial sequence
<220> FEATURE:
<223> OTHER INFORMATION: L03 lipase protein

<400> SEQUENCE: 6

```
Met Leu Leu Leu Ser Leu Leu Ser Ile Val Thr Leu Ala Val Ala Ser
1               5                   10                  15

Pro Leu Ser Val Glu Glu Tyr Ala Lys Ala Leu Glu Glu Arg Ala Val
            20                  25                  30

Thr Val Ser Ser Ser Glu Leu Asn Asn Phe Lys Phe Tyr Ile Gln His
        35                  40                  45

Gly Ala Ala Ala Tyr Cys Asn Ser Glu Thr Ala Ala Gly Ala Lys Val
    50                  55                  60

Thr Cys Ser Gly Asn Gly Cys Pro Glu Val Glu Ala Asn Gly Val Thr
65                  70                  75                  80

Val Val Ala Ser Phe Thr Gly Thr Lys Thr Gly Ile Gly Gly Tyr Val
                85                  90                  95

Ala Thr Asp Asn Ala Arg Lys Glu Ile Val Leu Ser Phe Arg Gly Ser
            100                 105                 110

Ile Asn Ile Arg Asn Trp Leu Thr Asn Leu Asp Phe Gly Gln Asp Asp
        115                 120                 125

Cys Ser Leu Thr Ser Gly Cys Gly Val His Ser Gly Phe Gln Arg Ala
    130                 135                 140

Trp Glu Glu Ile Ala Asp Asn Leu Thr Ala Ala Val Ala Lys Ala Lys
145                 150                 155                 160

Thr Ala Asn Pro Asp Tyr Lys Val Val Ala Thr Gly His Ser Leu Gly
```

```
                      165                 170                 175
Gly Ala Val Ala Thr Leu Ala Gly Ala Asn Leu Arg Val Gly Gly Thr
            180                 185                 190

Pro Leu Asp Ile Tyr Thr Tyr Gly Ser Pro Arg Val Gly Asn Ala Glu
        195                 200                 205

Leu Ala Ala Phe Val Ser Asn Gln Thr Gly Gly Glu Phe Arg Val Thr
    210                 215                 220

His Gly Asp Asp Pro Val Pro Arg Leu Pro Pro Leu Ile Phe Gly Tyr
225                 230                 235                 240

Arg His Thr Ser Pro Glu Tyr Trp Leu Asp Gly Ser Gly Gly Asp Lys
                245                 250                 255

Ile Asp Tyr Thr Ile Asn Asp Ile Lys Val Cys Glu Gly Ala Ala Asn
            260                 265                 270

Leu Gln Cys Asn Gly Gly Thr Leu Gly Leu Asp Ile Ala Ala His Leu
        275                 280                 285

His Tyr Phe Gln Ala Thr Asp Ala Cys Asn Ala Gly Gly Phe Ser Trp
    290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
                325                 330                 335

Glu Tyr Val Lys Asn Asn Gln Ala Arg Ser
            340                 345

<210> SEQ ID NO 7
<211> LENGTH: 1038
<212> TYPE: DNA
<213> ORGANISM: Artificial sequence
<220> FEATURE:
<223> OTHER INFORMATION: DNA L04 lipase gene

<400> SEQUENCE: 7
atgcttctcc tctccctcct ctccattgtc accctcgctg ttgcttctcc tctgtccgtt      60
gaggagtacg ccaaggccct cgaggagcgt gccgtcaccg tctcctcctc cgagctcaac     120
aacttcaagt tctacatcca gcacggtgct gctgcctact gcaactccga gactgctgct     180
ggtgccaacg tcacctgctc tggcaacggc tgccccgagg ttgaggccaa cggtgtcacc     240
gttgttgcct ccttcaccgg taccaagacc ggtatcggtg gctacgtcgc caccgacaac     300
gcccgcaagg agatcgtcct ctccttccgt ggcagcatca acatccgcaa ctggctgacc     360
aacctggact tcggccagga tgactgctct ctgacctccg gctgcggtgt ccactccggt     420
ttccagcgtg cctgggagga gattgccgac aacttgactg ctgctgttgc caaggccaag     480
actgccaacc ccgactacaa ggttgttgcc actggccact ctcttggtgg tgctgttgcc     540
actctggctg gtgccaacct ccgtgtcggt ggtaccccc tcgacatcta cacctacggc     600
tctcctcgtg tcggcaacgc cgagcttgct gctttcgtct ccaaccaggc tggtggtgag     660
ttccgtgtca cccacggtga tgaccccgtc ccccgtcttc ctcctctgat cttcggctac     720
cgccacacct cccccgagta ctggctcgat ggcagcggtg gtgacaagat cgactacacc     780
atcaacgaca tcaaggtctg cgagggtgct gccaacctgc agtgcaacgg tggtaccctg     840
ggtctcgaca ttgctgctca cctgcactac ttccaggcca tgatgcctg caacgccggt     900 ggtttcagct ggcgccgcta ccgctctgct gagagcgttg acaagcgtgc caccatgact     960
gatgctgagc tcgagaagaa gctcaacagc tacgtgcaga tggacaagga gtacgtcaag    1020
aacaaccagg ctcgctcc                                                   1038
```

<210> SEQ ID NO 8
<211> LENGTH: 346
<212> TYPE: PRT
<213> ORGANISM: Artificial sequence
<220> FEATURE:
<223> OTHER INFORMATION: L04 lipase protein

<400> SEQUENCE: 8

| | | | | | | | | | | | | | | | |
|---|---|---|---|---|---|---|---|---|---|---|---|---|---|---|---|
| Met | Leu | Leu | Leu | Ser | Leu | Leu | Ser | Ile | Val | Thr | Leu | Ala | Val | Ala | Ser |
| 1 | | | | 5 | | | | | 10 | | | | | 15 | |
| Pro | Leu | Ser | Val | Glu | Glu | Tyr | Ala | Lys | Ala | Leu | Glu | Glu | Arg | Ala | Val |
| | | | 20 | | | | | 25 | | | | | 30 | | |
| Thr | Val | Ser | Ser | Ser | Glu | Leu | Asn | Asn | Phe | Lys | Phe | Tyr | Ile | Gln | His |
| | | | 35 | | | | | 40 | | | | | 45 | | |
| Gly | Ala | Ala | Ala | Tyr | Cys | Asn | Ser | Glu | Thr | Ala | Ala | Gly | Ala | Asn | Val |
| | 50 | | | | | 55 | | | | | 60 | | | | |
| Thr | Cys | Ser | Gly | Asn | Gly | Cys | Pro | Glu | Val | Glu | Ala | Asn | Gly | Val | Thr |
| 65 | | | | | 70 | | | | | 75 | | | | | 80 |
| Val | Val | Ala | Ser | Phe | Thr | Gly | Thr | Lys | Thr | Gly | Ile | Gly | Gly | Tyr | Val |
| | | | | 85 | | | | | 90 | | | | | 95 | |
| Ala | Thr | Asp | Asn | Ala | Arg | Lys | Glu | Ile | Val | Leu | Ser | Phe | Arg | Gly | Ser |
| | | | 100 | | | | | 105 | | | | | 110 | | |
| Ile | Asn | Ile | Arg | Asn | Trp | Leu | Thr | Asn | Leu | Asp | Phe | Gly | Gln | Asp | Asp |
| | | | 115 | | | | | 120 | | | | | 125 | | |
| Cys | Ser | Leu | Thr | Ser | Gly | Cys | Gly | Val | His | Ser | Gly | Phe | Gln | Arg | Ala |
| | 130 | | | | | 135 | | | | | 140 | | | | |
| Trp | Glu | Glu | Ile | Ala | Asp | Asn | Leu | Thr | Ala | Ala | Val | Ala | Lys | Ala | Lys |
| 145 | | | | | 150 | | | | | 155 | | | | | 160 |
| Thr | Ala | Asn | Pro | Asp | Tyr | Lys | Val | Val | Ala | Thr | Gly | His | Ser | Leu | Gly |
| | | | | 165 | | | | | 170 | | | | | 175 | |
| Gly | Ala | Val | Ala | Thr | Leu | Ala | Gly | Ala | Asn | Leu | Arg | Val | Gly | Gly | Thr |
| | | | 180 | | | | | 185 | | | | | 190 | | |
| Pro | Leu | Asp | Ile | Tyr | Thr | Tyr | Gly | Ser | Pro | Arg | Val | Gly | Asn | Ala | Glu |
| | | | 195 | | | | | 200 | | | | | 205 | | |
| Leu | Ala | Ala | Phe | Val | Ser | Asn | Gln | Ala | Gly | Gly | Glu | Phe | Arg | Val | Thr |
| | 210 | | | | | 215 | | | | | 220 | | | | |
| His | Gly | Asp | Asp | Pro | Val | Pro | Arg | Leu | Pro | Pro | Leu | Ile | Phe | Gly | Tyr |
| 225 | | | | | 230 | | | | | 235 | | | | | 240 |
| Arg | His | Thr | Ser | Pro | Glu | Tyr | Trp | Leu | Asp | Gly | Ser | Gly | Gly | Asp | Lys |
| | | | | 245 | | | | | 250 | | | | | 255 | |
| Ile | Asp | Tyr | Thr | Ile | Asn | Asp | Ile | Lys | Val | Cys | Glu | Gly | Ala | Ala | Asn |
| | | | 260 | | | | | 265 | | | | | 270 | | |
| Leu | Gln | Cys | Asn | Gly | Gly | Thr | Leu | Gly | Leu | Asp | Ile | Ala | Ala | His | Leu |
| | | | 275 | | | | | 280 | | | | | 285 | | |
| His | Tyr | Phe | Gln | Ala | Thr | Asp | Ala | Cys | Asn | Ala | Gly | Gly | Phe | Ser | Trp |
| | 290 | | | | | 295 | | | | | 300 | | | | |
| Arg | Arg | Tyr | Arg | Ser | Ala | Glu | Ser | Val | Asp | Lys | Arg | Ala | Thr | Met | Thr |
| 305 | | | | | 310 | | | | | 315 | | | | | 320 |
| Asp | Ala | Glu | Leu | Glu | Lys | Lys | Leu | Asn | Ser | Tyr | Val | Gln | Met | Asp | Lys |
| | | | | 325 | | | | | 330 | | | | | 335 | |
| Glu | Tyr | Val | Lys | Asn | Asn | Gln | Ala | Arg | Ser | | | | | | |
| | | | 340 | | | | | 345 | | | | | | | |